United States Patent
Ou et al.

(10) Patent No.: US 7,132,296 B2
(45) Date of Patent: Nov. 7, 2006

(54) METHOD FOR ASSAYING THE ANTIOXIDANT CAPACITY OF A SAMPLE

(75) Inventors: Boxin Ou, Stoughton, MA (US); Dejian Huang, Randolph, MA (US); Maureen H. Woodill, Hyannis, MA (US)

(73) Assignee: Medical Products Manufacturing, LLC, Wareham, MA (US)

( * ) Notice: Subject to any disclaimer, the term of this patent is extended or adjusted under 35 U.S.C. 154(b) by 354 days.

(21) Appl. No.: 10/077,018

(22) Filed: Feb. 15, 2002

(65) Prior Publication Data

US 2003/0162297 A1    Aug. 28, 2003

(51) Int. Cl.
*G01N 33/00* (2006.01)

(52) U.S. Cl. .................. 436/177; 436/172; 436/164

(58) Field of Classification Search .............. 436/177, 436/172, 164
See application file for complete search history.

(56) References Cited

U.S. PATENT DOCUMENTS

| | | | | |
|---|---|---|---|---|
| 4,727,064 A | | 2/1988 | Pitha | 514/58 |
| 5,395,755 A | * | 3/1995 | Thorpe et al. | 435/28 |
| 6,060,324 A | | 5/2000 | Naguib | 436/71 |
| 6,114,177 A | | 9/2000 | Naguib | 436/172 |
| 6,429,021 B1 | * | 8/2002 | Qian et al. | 436/162 |

OTHER PUBLICATIONS

Ghiselli et al., "Total Antioxidant Capacity as a Tool to Assess Redox Status: Critical View and Experimental Data", Forum: Oxidative Stress Status, Free Radical Biology & Medicine, vol. 29, No. 11, (2000) pp. 1106-1114.

Prior et al., "In Vivo Total Antioxidant Capacity: Comparison of Different Analytical Methods", Forum: Oxidative Stress Status, Free Radical Biology & Medicine, vol. 27, Nos. 11/12, (1999), pp. 1173-1181.

Y.M.A. Naguib, "A Fluorometric Method for Measurement of Oxygen Radical-Scavenging Activity of Water-Soluble Antioxidants" Analytical Biochemistry 284, (2000) pp. 93-98.

Y.M.A. Naguib, "A Fluorometric Method for Measurement of Peroxyl Radical Scavenging Activities of Lipophilic Antioxidants" Analytical Biochemistry 265, (1998) pp. 290-298.

Y.M.A. Naguib, "Antioxidant Activities of Astaxanthin and Related Carotenoids" J. Agric. Food Chem, 48 (2000) pp. 1150-1154.

Sánchez-Moreno et al., "A Procedure to Measure the Antiradical Efficiency of Polyphenols", J. Sci Food Agric, 76 (1998), pp. 270-276.

Re et al., "Antioxidant Activity Applying an Improved ABTS Radical Cation Decolorization Assay", Free Radical Biology & Medicine, vol. 26, Nos. 9/10, (1999) pp. 1231-1237.

(Continued)

*Primary Examiner*—Monique T. Cole
(74) *Attorney, Agent, or Firm*—Iandiorio & Teska

(57) ABSTRACT

A method of assaying the antioxidant capacity of a sample, the method including preparing an extraction solution including a solubility enhancing compound, adding the sample to the extraction solution, extracting the antioxidants present in the sample, adding a fluorescent probe to the extract, adding a free radical generator to the extract, detecting the fluorescence intensity decay of the probe in the presence of the sample over time, and calculating the antioxidant capacity of the sample based on the fluorescence intensity decay of the probe in the presence of the sample.

58 Claims, 14 Drawing Sheets

OTHER PUBLICATIONS

Wang et al., "Total Antioxidant Capacity of Fruits", J. Agric. Food Chem., 44 (1996) pp. 701-705.

Cao et al., Abstract of "Oxygen-radical absorbance capacity assay for antioxidants", Free Radical Biology and Medicine, vol. 14, Issue 3, (Mar. 1993) pp. 303-311.

Frankel et al., "Interfacial Phenomena in the Evaluation of Antioxidants: Bulk Oils vs Emulsions", J. Agric. Food Chem., 42 (1994) pp. 1054-1059.

Ghiselli et al., "A Fluorescence-Based Method for Measuring Total Plasma Antioxidant Capability" Free Radical Biology & Medicine, vol. 18, No. 1, (1995) pp. 29-36.

Cao et al., "Antioxidant Capacity of Tea and Common Vegetables", J. Agric. Food Chem., 44 (1996) pp. 3426-3431.

Ehlenfeldt et al., "Oxygen Radical Absorbance Capacity (ORAC) and Phenolic and Anthocyanin Concentrations in Fruit and Leaf Tissues of Highbush Blueberry", J. Agric. Food Chem., 49 (2001) pp. 2222-2227.

* cited by examiner

FIG. 5

Station C — 230

| | 1 | 2 | 3 | 4 | 5 | 6 | 7 | 8 | 9 | 10 | 11 | 12 |
|---|---|---|---|---|---|---|---|---|---|---|---|---|
| A | sample1 0 | sample1 40.000 | sample1 80.000 | sample1 160.00 | sample1 320.00 | sample9 0 | sample9 40.000 | sample9 80.000 | sample9 160.00 | sample9 320.00 | BLK | Trolox1 6.2500 |
| B | sample2 0 | sample2 40.000 | sample2 80.000 | sample2 160.00 | sample2 320.00 | sample10 0 | sample10 40.000 | sample10 80.000 | sample10 160.00 | sample10 320.00 | BLK | Trolox2 12.500 |
| C | sample3 0 | sample3 40.000 | sample3 80.000 | sample3 160.00 | sample3 320.00 | sample11 0 | sample11 40.000 | sample11 80.000 | sample11 160.00 | sample11 320.00 | BLK | Trolox3 25.000 |
| D | sample4 0 | sample4 40.000 | sample4 80.000 | sample4 160.00 | sample4 320.00 | sample12 0 | sample12 40.000 | sample12 80.000 | sample12 160.00 | sample12 320.00 | BLK | Trolox4 50.000 |
| E | sample5 0 | sample5 40.000 | sample5 80.000 | sample5 160.00 | sample5 320.00 | sample13 0 | sample13 40.000 | sample13 80.000 | sample13 160.00 | sample13 320.00 | BLK | Trolox4 50.000 |
| F | sample6 0 | sample6 40.000 | sample6 80.000 | sample6 160.00 | sample6 320.00 | sample14 0 | sample14 40.000 | sample14 80.000 | sample14 160.00 | sample14 320.00 | BLK | Trolox3 25.000 |
| G | sample7 0 | sample7 40.000 | sample7 80.000 | sample7 160.00 | sample7 320.00 | sample15 0 | sample15 40.000 | sample15 80.000 | sample15 160.00 | sample15 320.00 | BLK | Trolox2 12.500 |
| H | sample8 0 | sample8 40.000 | sample8 80.000 | sample8 160.00 | sample8 320.00 | sample16 0 | sample16 40.000 | sample16 80.000 | sample16 160.00 | sample16 320.00 | BLK | Trolox1 6.2500 |

FIG. 6

Station C

| | 1 | 2 | 3 | 4 | 5 | 6 | 7 | 8 | 9 | 10 | 11 | 12 |
|---|---|---|---|---|---|---|---|---|---|---|---|---|
| A | BLK | Trolox1 6.2500 | sample1 40.000 | sample1 80.000 | sample1 160.00 | sample1 320.00 | sample9 40.000 | sample9 80.000 | sample9 160.00 | sample9 320.00 | control | BLK |
| B | BLK | Trolox2 12.500 | sample2 40.000 | sample2 80.000 | sample2 160.00 | sample2 320.00 | sample10 40.000 | sample10 80.000 | sample10 160.00 | sample10 320.00 | control | BLK |
| C | BLK | Trolox3 25.000 | sample3 40.000 | sample3 80.000 | sample3 160.00 | sample3 320.00 | sample11 40.000 | sample11 80.000 | sample11 160.00 | sample11 320.00 | control | BLK |
| D | BLK | Trolox4 50.000 | sample4 40.000 | sample4 80.000 | sample4 160.00 | sample4 320.00 | sample12 40.000 | sample12 80.000 | sample12 160.00 | sample12 320.00 | control | BLK |
| E | BLK | Trolox4 50.000 | sample5 40.000 | sample5 80.000 | sample5 160.00 | sample5 320.00 | sample13 40.000 | sample13 80.000 | sample13 160.00 | sample13 320.00 | control | BLK |
| F | BLK | Trolox3 25.000 | sample6 40.000 | sample6 80.000 | sample6 160.00 | sample6 320.00 | sample14 40.000 | sample14 80.000 | sample14 160.00 | sample14 320.00 | control | BLK |
| G | BLK | Trolox2 12.500 | sample7 40.000 | sample7 80.000 | sample7 160.00 | sample7 320.00 | sample15 40.000 | sample15 80.000 | sample15 160.00 | sample15 320.00 | control | BLK |
| H | BLK | Trolox1 6.2500 | sample8 40.000 | sample8 80.000 | sample8 160.00 | sample8 320.00 | sample16 40.000 | sample16 80.000 | sample16 160.00 | sample16 320.00 | control | BLK |

274, 280, 282, 284, 286, 288, 290, 292, 294, 296, 298, 300, 302

METHOD FOR ASSAYING THE ANTIOXIDANT CAPACITY OF A SAMPLE

FIELD OF THE INVENTION

This invention relates to an improved method for assaying the antioxidant capacity of a sample.

BACKGROUND OF THE INVENTION

Molecules are composed of atoms bonded together. This bonding process is accomplished by the sharing of electrons. When two atoms come together and their electrons pair up, a bond is created. Generally, only two electrons can exist in one bond. Paired electrons are quite stable and almost all electrons in the human body exist in a paired state. However, when a bond is broken, the electrons can either stay together or split up. If the electrons stay together, both electrons go to one of the atoms and none go to the other atom. In this case the molecular fragments are called ions, which are electrically charged and typically not harmful to humans or other animals. For example, sodium chloride, NaCl, can split up into a sodium cation ($Na^+$) and a chloride anion ($Cl^-$). But, if the electrons split up when a bond is broken, one electron will go to each atom, creating two molecules with unpaired electrons, called free radicals. The unpaired electrons of these free radicals are highly energetic and unstable and seek out other electrons with which to pair with. As a result, free radicals steal electrons from other molecules. The process of stealing electrons from other electron pairs is what makes free radicals dangerous because it causes oxidation, or loss of electrons, to the molecule it attacks, leaving an unstable, highly energetic molecule. Since most electrons exist in a paired state, free radicals often end up reacting with paired electrons and create still more free radicals. Only when a free radical pairs up with another free radical is the free radical terminated.

Antioxidants, or free radical scavengers, function by offering easy electron targets for free radicals. In absorbing a free radical, antioxidants "trap", or de-energize and stabilize the lone free-radical electron and make it stable enough not be harmful.

As such, antioxidants provide a defense against free radicals which cause cell oxidation in humans and other animals. Presently, there is overwhelming evidence to indicate that free radicals cause oxidative damage to lipids, proteins and nucleic acids. Antioxidants can play an important role in the prevention of a number of diseases including cancer, heart, vascular, and neurogenitive diseases. See *Oxygen-Radical Absorbance Capacity for Antioxidants*, Cao, G., Free Radical Biol. Med. Vol. 14, (1993), incorporated herein in its entirety by this reference.

Many foods contain substantial quantities of antioxidants. The need to effectively measure the antioxidant capacity of such foods is of significant importance to people who are trying to prevent diseases caused by free radicals, to manufacturers of foods alleged to contain high antioxidant capacities, and to the scientific community. Moreover, in the medical community, measuring the antioxidant capacity of blood and serum can be useful in prevention of disease. Accordingly, many food, vitamin and supplement suppliers seek to test the antioxidant capacity of their various products. In addition, biological samples are often tested to determine their antioxidant capacity.

In 1993, the Oxygen Radical Absorbance Capacity (ORAC) assay was developed to test the antioxidant capacity of a given sample. See *Oxygen-Radical Absorbance Capacity for Antioxidants* cited above. And, in 1998, an automated device, the Roche COBAS FARA II analyzer, was placed on the market to test samples according to the ORAC assay. Moreover, significant research has been performed to determine the antioxidant capacity of samples using the ORAC assay. See, e.g. *Oxygen Radical Absorbance Capacity (ORAC) and Phenolic and Anthocyanin Concentrations in Fruit and Leaf Tissues of Highbush Blueberry*, Ehlenfeldt, M. and Prior, R., J. Agric. Food Chem., 49, pp. 2222–2227 (2001); *In Vivo Total Antioxidant Capacity: Comparison of Different Analytical Methods*, Prior, R. and Cao, G., Free Radical Biol. Med., Vol. 27, Nos. 11/12, pp. 1173–1181 (1999); *Total Antioxidant Capacity of Fruits*, Wang, H., Cao, G., Prior, R., J. Agric. Food Chem., 44, pp. 701–705 (1996); and *Antioxidant Capacity of Tea and Common Vegetables*, Cao, G., Sofic, E., and Prior, R., J. Agric. Food Chem., 44, pp. 3426–3431 (1996), all incorporated herein in their entirety by this reference.

Since about 1998, the inventors hereof have used the COBAS FARA II to test various samples according to the ORAC assay. In performing the ORAC assay numerous times, the inventors hereof detected and herein delineate solutions to numerous problems associated with the conventional ORAC assay.

In accordance with the published ORAC assay, a sample such as fresh fruit, blood serum, or an additive or supplement in powder form is prepared for extraction and extracted first in water and then in acetone. A protein based fluorescent probe, namely B-phycoerythrin (B-PE) is then added to the extract. A standard, having high antioxidant capacity, such as diluted grape seed extract (GSE) or TROLOX® (6-hydroxy-2,5,7,8-tetramethylchroman-2-carboxylic acid), a water soluble analog of vitamin E, is added to the extract to provide a comparison of the antioxidant capacity of the sample to the standard. The extract, the standard, and a blank sample are then loaded into the COBAS FARA II device and an initial fluorescence emission of the probe is taken. Next, AAPH, (2,2'-azobis (2-amidino-propane) dihydrochloride), which generates free radicals upon heating, is added to the extract of the sample and the standard and fluorescence emission readings are taken until a zero value is reached for the extract of the sample. To measure the protective effect of an antioxidant using the ORAC assay, the area under the fluorescence decay curve (AUC) of the sample is calculated and compared to that of the blank in which no antioxidant is present.

One problem with this prior art assay is that samples including high levels of lipid soluble antioxidants are not correctly rated because of their insolubility in aqueous media. Further, samples including both lipid soluble antioxidants and water-soluble antioxidants are not correctly rated.

Another problem with the prior art ORAC assay is that the probe used was B-PE. This protein probe was found to interact with the sample in adverse ways and generated false low readings. Moreover, because B-PE is manufactured from a microorganism, it was found to vary in purity and composition from lot to lot. In addition, B-PE is highly photosensitive which is a severe drawback when fluorescence intensity decay is used in the assay in that B-PE requires special handling.

Another problem with the prior art ORAC assay is that since only one standard is used, calculating the antioxidant capacity of the sample based on the fluorescence intensity decay of the probe in both the sample and the standard incorrectly assumes that a direct ratio between the antioxidant capacity of the standard and the sample could be made. This, however, is not true.

Still another problem with the prior art ORAC assay is that percloric acid was added to biological samples to separate proteins from the sample. The inventors hereof discovered that percloric acid, itself a strong oxidizing agent, yielded false low antioxidant capacity readings.

Finally, the prior art ORAC procedure involved a long dwell time of up to 75 minutes.

SUMMARY OF THE INVENTION

It is therefore an object of this invention to provide an improved method of assaying the antioxidant capacity of a sample.

It is a further object of this invention to provide such a method which accurately measures the antioxidant capacity of a sample even if it has a high level of lipid soluble antioxidants.

It is a further object of this invention to provide such a method which accurately measures the antioxidant capacity of a sample having both high level of lipid soluble antioxidants and water soluble antioxidants.

It is a further object of this invention to a provide a probe which does not interact with the sample.

It is a further object of this invention to provide such a method using a probe which is more stable.

It is a further object of this invention to provide such a method in which the probe is consistent in purity from lot to lot.

It is a further object of this invention to provide such a method using a probe which is not photosensitive.

It is a further object of this invention to provide such a method in which a plurality of standards are used to accurately measure the antioxidant capacity of a sample.

It is a further object of this invention to provide such a method which uses a non-chemical means to remove proteins from a sample.

It is a further object of this invention to provide such method which is a more time efficient method for assaying the antioxidant capacity of a sample.

This invention results from the realization that an improved method for assaying the antioxidant capacity of a sample, in the preferred embodiment, can be achieved by preparing an extraction solution which includes a solubility enhancing compound; by using a unique non-protein probe which does not interact with the sample, and which is consistently pure, and which is not photosensitive; by employing a plurality of standards which correctly account for the ratio between the antioxidant capacity of the standard and the sample; by using non-chemical means to remove the proteins thereby eliminating any interaction with the sample; and by increasing the concentration of AAPH to decrease the dwell time.

This invention features a method of assaying the antioxidant capacity of a sample, the method including preparing an extraction solution including a solubility enhancing compound, adding the sample to the extraction solution, extracting the antioxidants present in the sample, adding a fluorescent probe to the extract, detecting the fluorescence intensity decay of the probe in the presence of the sample over time, and calculating the antioxidant capacity of the sample based on the fluorescence intensity decay of the probe in the presence of the sample.

The method of assaying the antioxidant capacity in accordance with this invention may include solubility enhancing solution having a high polarity solvent and a low polarity solvent wherein the solubility enhancing compound enhances the solubility of lipid soluble antioxidants present in the sample in the high polarity solvent. Ideally, the high polarity solvent is water, and the low polarity solvent is selected from acetone, butane, methanol, acetonitrile and ethanol. In one embodiment, the solubility enhancing compound is cyclodextrine and derivatives thereof. The amount of the high polarity solvent may be equal to or approximately equal to the amount of low polarity solvent. The solubility enhancing compound may be 1% to 40% of the solution.

The method of assaying the antioxidant capacity in accordance with this invention may also include a non-protein probe which is a hydrogen atom donor probe. Preferably, the hydrogen atom donor probe is fluorescein and derivatives thereof.

This invention also features a method of assaying the antioxidant capacity, the method including adding the probe to a plurality of standards each having a known antioxidant capacity, and detecting the fluorescence intensity decay of the probe in the presence of each standard over time. Preferably, the calculation step includes comparing the fluorescence intensity decay of the probe in the presence of sample with the fluorescence intensity decay of the probe in the presence of each standard. In a preferred embodiment there are four standards, with the concentration of the standards ranges from 10 µM to 100 µM. Ideally, each standard is Trolox. The preparation step may include removing any proteins present in the sample by using non-chemical means to remove the proteins, such as an ultra-filtration technique. A free radical generator precursor is added to the probe/extract mixture, such as AAPH above 4 mM. The preferred concentration of AAPH is 12.8 mM.

This invention also features a method of assaying the antioxidant capacity in which a microplate fluorescence reader is used to detect the intensity decay of the probe in the presence of the sample over time. Ideally, the microplate fluorescence reader is a FL600 microplate fluorescence reader. An automatic pipetting system may be used to dilute the sample, such as a Precision 2000 automatic pipetting system. In a preferred embodiment, the sample is automatically diluted with a buffer solution to a concentration of the sample to buffer in the range of 1:40 to 1:320. Ideally, the automatic pipetting system adds the fluorescent probe to the sample. The automatic pipetting system may also add the fluorescent probe to the plurality of standards. The automatic pipetting system may additionally add the free radical generator precursor to the probe/extract mixture.

This invention also features a method of assaying the antioxidant capacity of a sample including preparing an extraction solution, adding the sample to the solution, extracting the antioxidants present in the sample, adding a non-protein probe to the extract, detecting the fluorescence intensity decay of the non-protein probe in the presence of the sample over time, and calculating the antioxidant capacity of the sample based on the fluorescence intensity decay of the non-protein probe in the presence of the sample.

This invention further features a method of assaying the antioxidant capacity, the method including preparing an extraction solution including a solubility enhancing compound, adding the sample to the extraction solution, extracting the antioxidants present in the sample, adding a fluorescent probe to the extract, adding a free radical generator precursor to the extractor solution, detecting the fluorescence intensity decay of the probe in the presence of the sample over time, and calculating the antioxidant capacity of the sample based on the fluorescence intensity decay of the probe in the presence of the sample.

This invention further features a kit for assaying the antioxidant capacity of a sample including an extraction solution including a solubility enhancing compound to be added to a sample for extracting antioxidants present in the sample, and a fluorescent probe to be added to the extract. The extraction solution includes a high polarity solvent such as water and a low polarity solvent selected from the acetone, butane, methanol, acetonitrile and ethanol. The kit may include a solubility enhancing compound, such as cyclodextrin and derivatives thereof. The amount of the high polarity solvent may be equal to or approximately equal to the amount of low polarity solvent. Ideally, the solubility enhancing compound is 1% to 40% of the solution. The kit may include a non-protein probe which is a hydrogen atom donor probe, such as fluorescein, and may also include a plurality of standards each having a known antioxidant capacity so that the fluorescence intensity decay of the probe in the presence of each standard over time can be detected. There may be four standards, ranging from 10 µM to 100 µM. Ideally, the standard is Trolox. The kit may include adding a free radical generator precursor to be added to the probe/extract mixture, such as AAPH. In one embodiment, the concentration of the precursor is above 4 mM. Ideally, the concentration of the precursor is 12 mM.

BRIEF DESCRIPTION OF THE DRAWINGS

Other objects, features and advantages will occur to those skilled in the art from the following description of a preferred embodiment and the accompanying drawings, in which:

FIG. 5 is a schematic diagram of a multiple-well microplate located at one of the stations of a Precision 2000 automatic pipetting system showing one configuration of various samples, blank solutions, and standard solutions, in accordance with the subject invention;

FIG. 6 is a schematic diagram of a multiple-well microplate located at another station of the Precision 2000 automatic pipetting system showing one configuration of diluted samples, blank solutions, standard solutions, and control solutions in accordance with the subject invention;

DETAILED DESCRIPTION OF THE INVENTION

As explained in the Background of the Invention section above, antioxidants provide a defense against free radicals which cause oxidation in humans and other animals. Antioxidants can neutralize free radicals and play an important role in the prevention of a number of diseases. Many foods contain substantial quantities of antioxidants and the need to effectively measure the antioxidant capacity of such foods is of significant importance to people who are trying to prevent diseases caused by free radicals, manufacturers of foods alleged to contain high antioxidant capacities, and in the scientific community. Moreover, in the medical community, measuring the antioxidant capacity of blood and serum can be useful in the prevention of disease.

Figure 1:
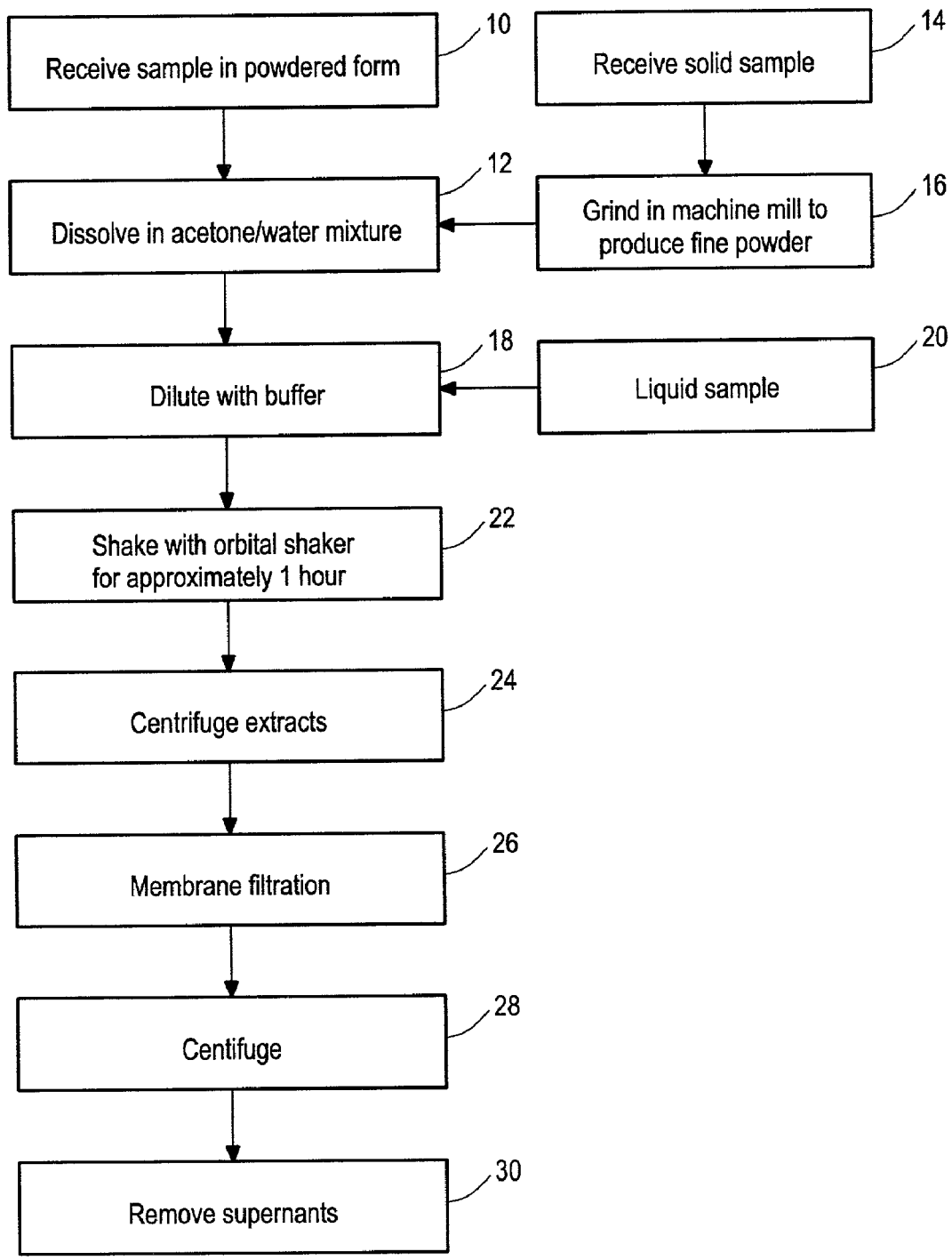
FIG. 1 is a schematic block diagram showing the primary steps associated with the preparation of a sample to be tested in accordance with the subject invention.

In accordance with the subject invention, samples for testing may be received either in powdered form or in coarse form. A sample is received in powdered form, step 10, FIG. 1. The sample is then dissolved in an acetone and water mixture, typically a 50% acetone and a 50% water mixture, step 12. If a coarse sample is received, step 14, it is ground in a machine mill to produce a fine powder, step 16. In either case, after the sample is dissolved in the acetone water mixture, the solution is diluted with a buffer, step 18. However, if the sample is liquid, such as blood serum, or any other bodily fluid, as shown at step 20, it is directly diluted with a buffer as shown in step 18. The solution is then shaken using an orbital shaker for approximately 1 hour, step 22. The extract solution is then centrifuged, step 24; membrane filtration is performed to remove any proteins (e.g. blood or serum samples), step 26; the extract is then centrifuged again, step 28; and the supernatant is removed for analysis, step 30. The sample is now ready for analysis with the COBAS FARA II analyzer (Roche Diagnostic System Inc., Branchburg, N.J.; emission filter 565 nm).

Figure 2:
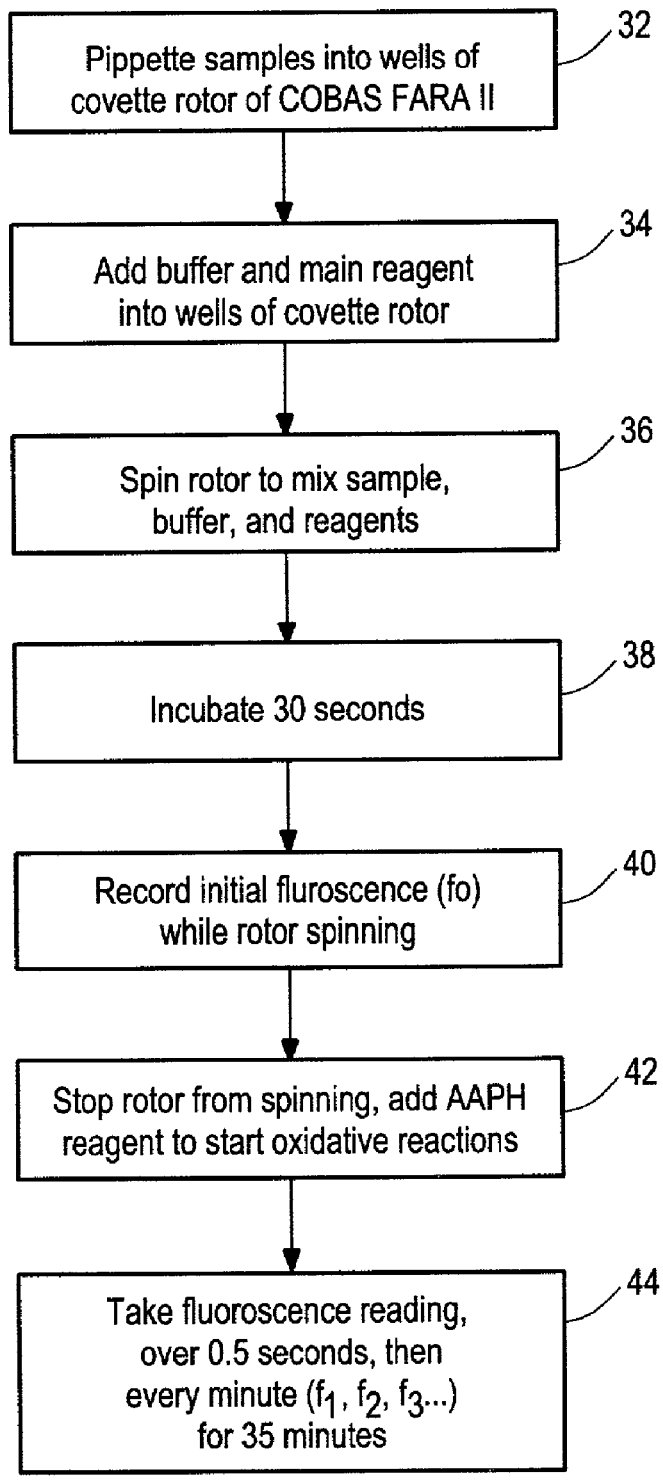
FIG. 2 is schematic block diagram showing the primary steps associated with analyzing the antioxidant capacity of a sample using the COBAS FARA II in accordance with the subject invention.

Using the COBAS FARA II analyzer, the sample is first pipetted into the COBAS FARA II tube, step 32, FIG. 2; a buffer and main reagent is then added into the wells of the covette rotor of the COBAS FARA II, step 34. The rotor is then spun to mix the sample buffer and reagents, step 36; the solution is then incubated for 30 seconds, step 38. An initial fluorescence ($f_o$) is taken while the rotor is spinning, step 40; the rotor is stopped from spinning and a sample of AAPH reagent is added to start the oxidative reaction, step 42; and fluorescence decay readings are taken every half second then every minute for thirty-five minutes ($f_1, f_2, f_3 \ldots$ step 44.

A FL600 microplate fluorescence reader (Bio-Tek Instruments, Inc., Winooski, Vt.) may also be used sample analysis. Ideally the FL600 microplate reader employs fluorescence filters with an excitation wavelength of 485±20 nm and an emission wavelength of 530±25 nm. The FL600 microplate fluorescence reader is controlled by software, such as KC4 3.0 (reversion 29). Sample dilution is performed by an automated liquid handler with a robotic multi-channel liquid handling system in which the samples are diluted in series. Preferably, a Precision 2000 automatic pipetting system managed by software, such as Precision Power software (version 1.0), (Bio-Tek Instruments, Inc., Winooski, Vt.) is employed.

Figure 3A:
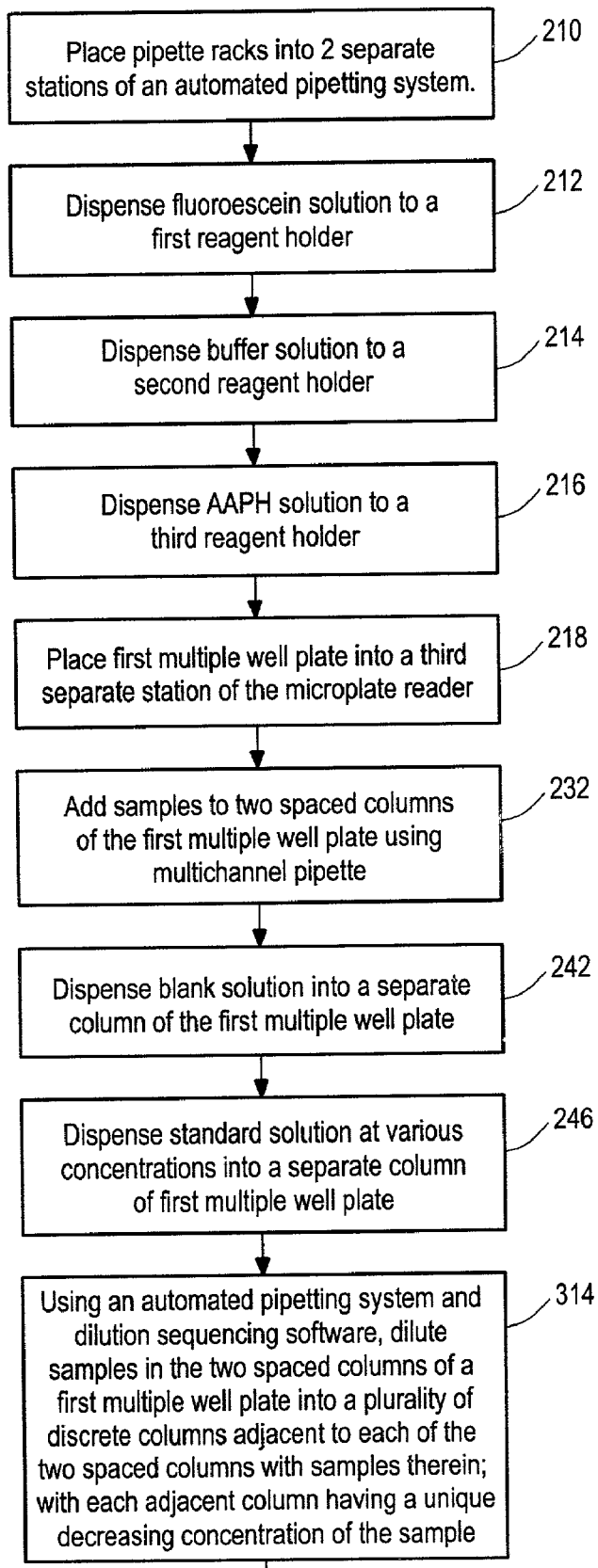
FIGS. 3A–3C are schematic diagrams showing the primary steps associated with analyzing the antioxidant capacity of a sample using an FL600 microplate fluorescence reader and a Precision 2000 automatic pipetting system.
Figure 4:
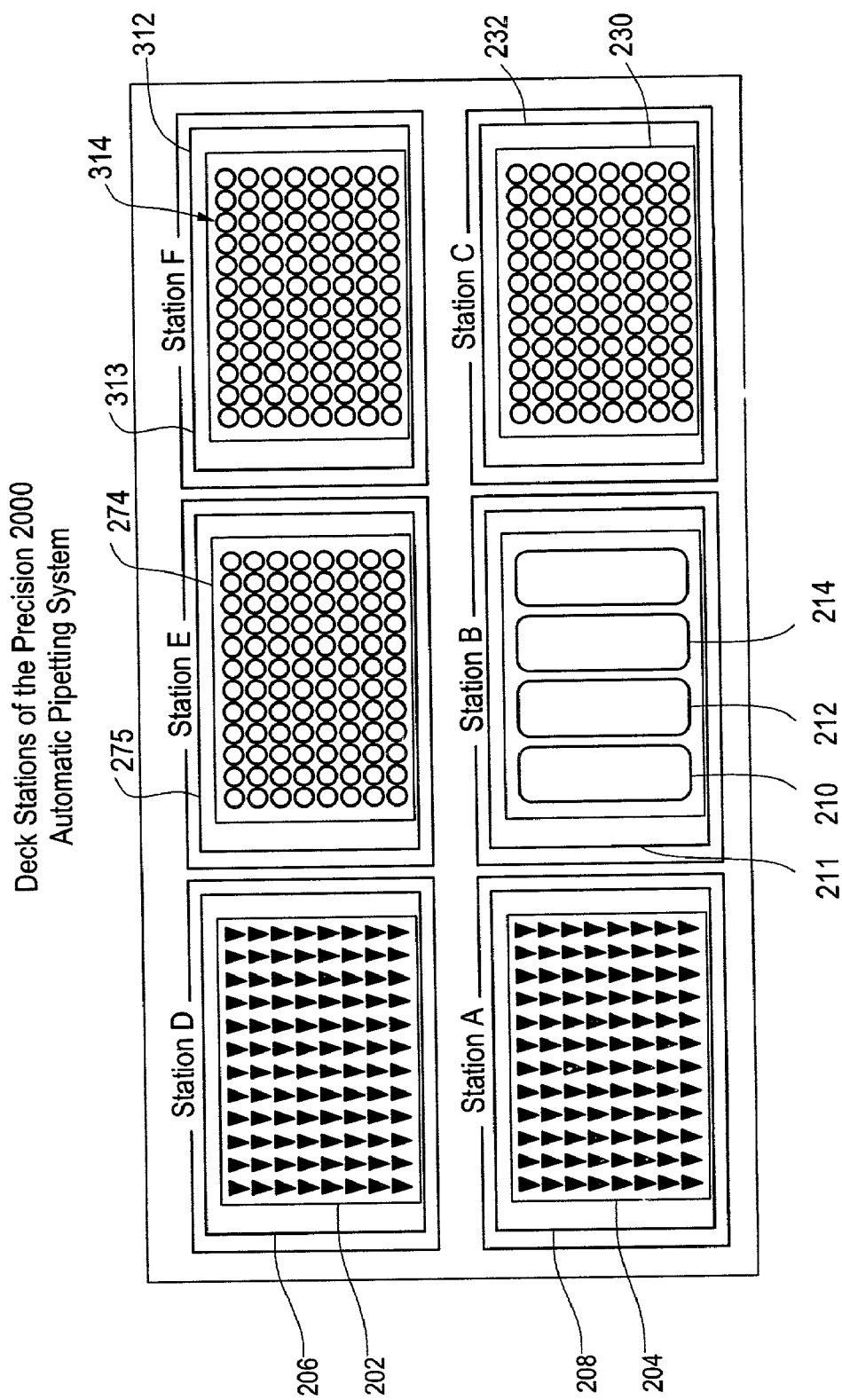
FIG. 4 is a schematic diagram showing one configuration of the deck station of the Precision 2000 automatic pipetting system in accordance with the subject invention.

Automated sample preparation begins by placing two pipette racks 202 and 204, FIG. 4 into two separate stations 206 and 208, respectively, of the Precision 2000 automatic pipetting system, step 210, FIG. 3A. In one example, 250 μL 96-pipette racks used. Fluorescein is then dispensed into first reagent holder 210, FIG. 4 located, in one example at station 211, step 212, FIG. 3A. Preferably, 50 mL $8.16 \times 10^{-5}$ mM fluorescein is placed in first reagent holder 210. A buffer solution is dispensed into second reagent holder 212, step 214, FIG. 3A. Ideally, 50 ml 75 mM phosphate buffer (pH 7.4) is added to second reagent holder 212, FIG. 4. AAPH solution is added to third reagent holder 216, FIG. 4, as shown by step 216, FIG. 3A. A first multiple-well plate 230, FIG. 4 is placed in third separate station 232 of the Precision 2000, step 218, FIG. 3A. Preferably, a 96-well polypropylene plate with a maximum well volume of 320 μL is used.

Samples are then manually added using a multi-channel pipette to two spaced columns 234 and 238 of first multiple-well plate 230, FIG. 5, indicated by step 232, FIG. 3A. In one example, eight samples are pipetted into first spaced column 234, FIG. 5 (wells A1-H1), and eight additional samples are pipetted into second spaced column 238 (wells A6-H6).

A blank solution is then dispensed into column 240, FIG. 5 of first multiple well plate 230, step 242, FIG. 3A. In one example, 200 μL of 75 mM phosphate buffer (blank) is dispensed into column 240, FIG. 5 (wells A11-H11).

A standard solution at various concentration is dispensed into separate column 244, FIG. 5 of first multiple well plate 230, step 246, FIG. 3A. In one example, a Trolox standard solution is added to column 244, FIG. 5 of first multiple well plate 230 (wells A12-H12). The various concentrations of Trolox standard solution in column 244, in one example, are be 6.25 μM (well A12), 12.5 μM (well B12), 25 μM (well C12), 50 μM (well D12), 50 μM (well E12), 25 μM (well F12), 12.5 μM (well G12), and 6.25 μM (well H12).

In order to perform series dilution of the samples in column 234 and 238 of first multiple well plate 230, FIG. 5, an automated pipetting system is used, such as a Precision 2000 managed by dilution sequencing software, such as Precision Power software (version 1.0). The samples in two spaced columns 234 and 238 are diluted into plurality of discreet columns 241, 243, 245, and 247, and 248, 250, 252, and 254, respectively, step 314, FIG. 3A. Ideally, each column of diluted sample adjacent to sample columns 234 and 238, FIG. 5 has a lower concentration of sample than the next. In one example, the sample series dilution of samples in columns 234 and 238 performed by the Precision 2000 controlled by the dilution sequencing software resulted in a dilution of 1:40 (sample to buffer) in columns 241 (wells A2 to H2) and column 248 (wells A7 to H7). Consecutive dilutions of 1:2, 1:2, and 1:2 are performed by the Precision 2000 to the samples in columns 241–247 and 248–254, respectively, by the Precision 2000. The result, in one example, is a series of diluted samples at ratios of 1:40, 1:80, 1:160, and 1:320, as shown in FIG. 5. Alternatively, any other desired lower dilution can be obtained by performing a series of 1:4 or 1:8 dilutions as after initial 1:40 dilution. Moreover, any other desired series of dilutions can be produced as needed.

Figure 3B:
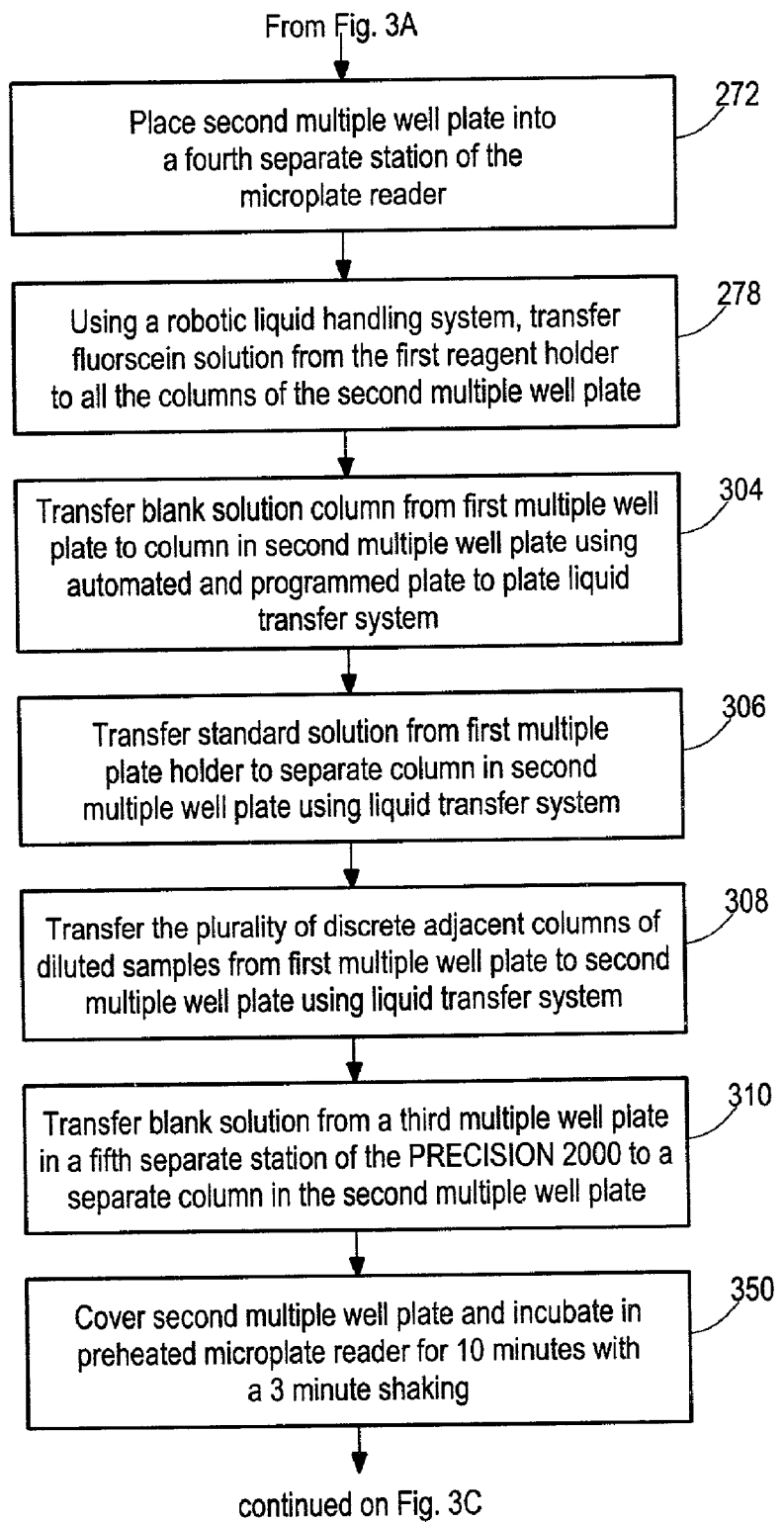

A second multiple well plate 274, FIG. 4 is placed into fourth separate station 312 of the Precision 2000, step 272, FIG. 3B. Second multiple-well plate 274 is needed to provide for an automated plate-to-plate transfer of the diluted samples from first multiple well plate 230 to second multiple well plate 274. In one example, a second 96-well polystyrene plate is placed in station E of the FL600 microplate reader. A fully automated plate-to-plate liquid transfer is programmed by the Precision Power software. The robotic liquid handling system of the Precision 2000 driven by the Precision Power software, transfers fluorescein from first reagent holder 210, FIG. 4, to all of the wells of second multiple well plate 274 located in station 275 (e.g., Station E) of the Precision 2000, step 278, FIG. 3B. In one example, 150 μL of fluorescein solution from reagent holder 210, FIG. 4 is transferred to all columns of first multiple well plate 274.

The blank solution in column 240 of first multiple well plate 230 is transferred to column 302 of second multiple well plate 274 using the automated and programmed plate-to-plate liquid transfer system described above, step 304, FIG. 3B. Ideally, 25 μL of blank solution is transferred from column 240 (wells A11-H11) of first multiple well plate 274, FIG. 5 to column 302 (wells A12-H12), FIG. 6 of second multiple well plate 274.

The standard solution (e.g. Trolox) in column 244 of first multiple well plate 230, FIG. 5, is transferred to column 282, FIG. 6, in second multiple well plate 274 via the plate-to-plate liquid transfer system, step 306, FIG. 3B.

The plurality of discrete adjacent columns of diluted samples (e.g., columns 241–247 and 248–254, FIG. 5) in first multiple well plate 230 are automatically transferred to a plurality of discrete adjacent columns in second multiple well plate 274 by the liquid transfer system, step 308, FIG. 3B. In one example, 25 μL of diluted sample solutions from the adjacent columns 241, 243, 245, and 247 in first multiple well plate 230, FIG. 5, are transferred to columns 284, 286, 288, and 290, respectively, of second multiple well plate 274. Similarly, 25 μL of diluted sample solutions from the adjacent columns 248, 250, 252, and 254, FIG. 5, in first multiple well plate 230, are transferred to columns 292, 294, 296, and 298, respectively, of second multiple well plate 274 by the Precision 2000 automatic pipetting system controlled by the dilution sequencing software.

The control solution from third multiple well plate 312, FIG. 4, located in fifth separate station 312 (e.g., Station F) of the Precision 2000 is transferred to separate column 300, FIG. 6, in second multiple well plate, step 310, FIG. 3B. In one example, 25 μL of 25 μM gallic acid is transferred from column 314 of third multiple well plate 312, FIG. 4, to column 300 of second multiple-well plate 274, FIG. 6.

Second multiple well plate 274 is then immediately covered and incubated in the preheated (37° C.) FL600 microplated fluorescence reader for ten minutes and provided with a three minute shaking, step 350, FIG. 3B. Second multiple well plate 274 is then transferred back to station 275 (e.g., Station E) of the FL6000 microplate fluorescence reader, step 354, FIG. 3C. AAPH is then transferred from third reagent holder 214, FIG. 4, to all of the columns of the second multiple well plate 274, FIG. 6, excluding columns 280 and 302 wherein the blank solutions are located, step 356, FIG. 3C. Hence, when the automated sample preparation is complete, the total volume for each well is ideally 200 µL.

Figure 3C:
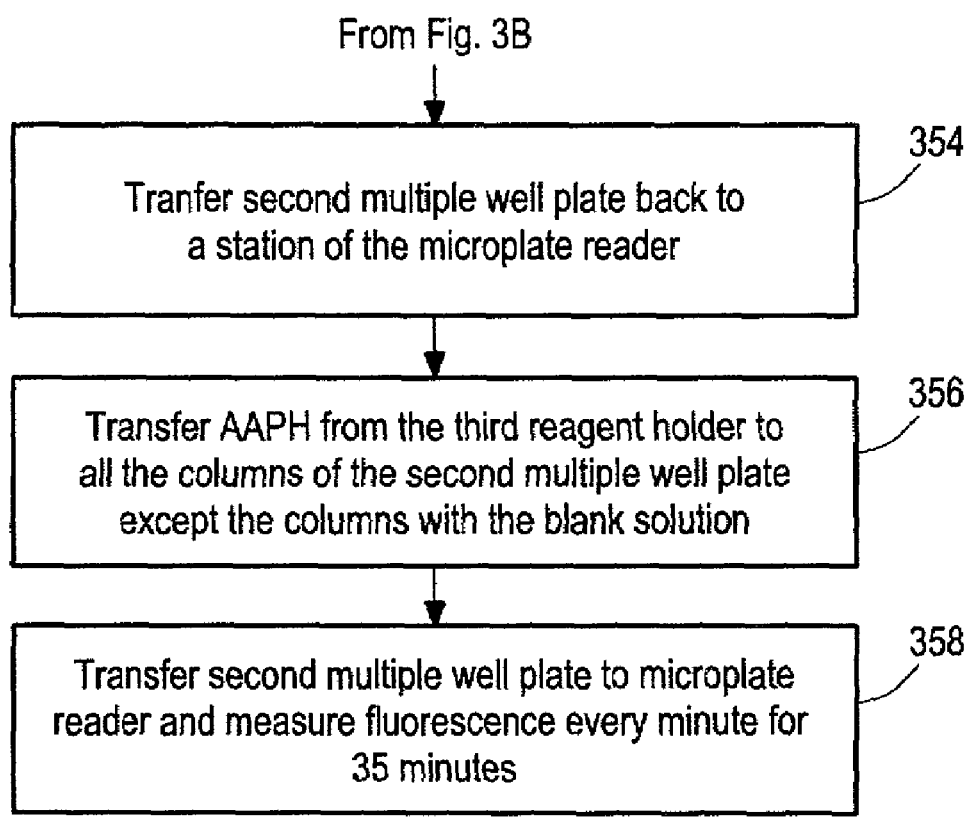

Second multiple well plate 274 is then transferred to FL6000 microplate fluorescence reader and fluorescence is measured every minute for thirty-five minutes, step 358, FIG. 3C.

FIG. 6 shows the layout of a typical 96-well plate used for a measurement with the FL600 microplate fluorescence reader. Although the samples, standard, and blank solutions are located at specific columns, in FIGS. 5 and 6, and the pipette racks, multiple well plates and reagent holders are located at specific stations in the Precision 2000, this is not a necessary limitation of the invention as any configuration of the various columns and stations may be used.

Figure 7:
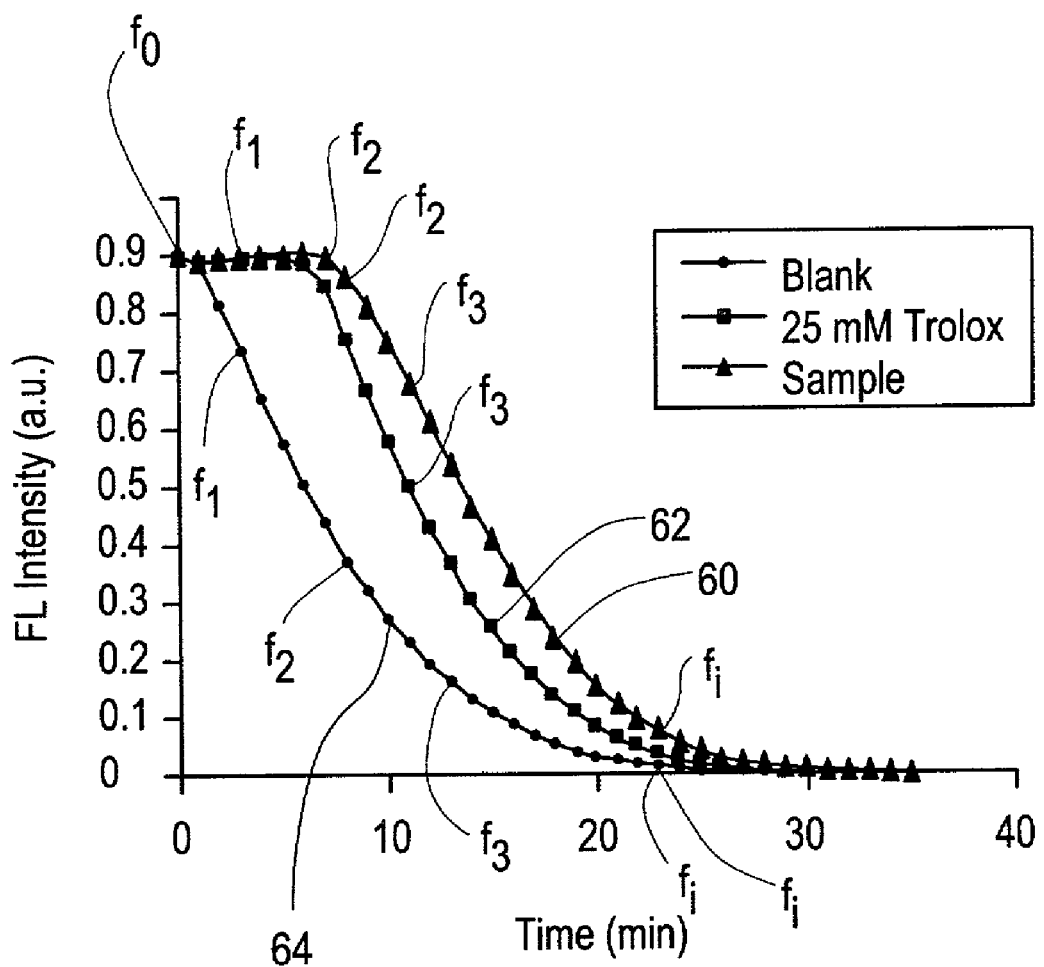
FIG. 7 is a graph showing the fluorescence intensity decay over time of a sample being tested, a standard, and a blank for a typical ORAC assay.

After the fluorescent readings are taken, the ORAC values are calculated by using a regression equation between standard concentration 62, FIG. 7, and the net area under the B-PE decay curve of sample 60. ORAC values are typically expressed in µmole Trolox equivalent per liter or per gram.

In accordance with the subject invention the area under the curve (AUC) for the sample, standard, and blank are calculated as:

$$AUC = 0.5 + f_1/f_0 + f_2/f_0 + f_3/f_0 + f_4/f_0 + \ldots + f_i/f_0 \quad (1)$$

Where $f_0$=initial fluorescence reading at 0 minute, and $f_i$ is the fluorescence reading at time i. Typically, equation (1) is solved and the data analyzed in an electronic spreadsheet such as Microsoft Excel or other similar products or computer programs. The AUC is calculated for sample 60, standard 62 and blank 64. The net AUC is obtained by subtracting the AUC of blank 64 from sample 60. The relative ORAC value for sample 60, expressed in Trolox equivalents is calculated as:

Relative ORAC value=$[(AUC_{sample}-AUC_{Blank})/(AUC_{Trolox}-AUC_{Blank})]\times$(molarity of Trolox/molarity of sample)  (2)

Accordingly, the ORAC value yields the antioxidant capacity of the sample can be found.

One problem with the prior art ORAC assays is that oil soluble antioxidants are not correctly rated because of their insolubility in aqueous media. Further, most analytical instruments used for antioxidant testing, such as the COBAS FARA II analyzer or FL600 microplate fluorescence reader are designed to handle only aqueous solutions. As a result, these prior art ORAC assays are less ideal for lipid or oil soluble samples. Moreover, most fat-soluble free radical precursors generate free radicals only at high temperature (>70° C.) at which many organic solvents evaporate and create environmental hazards. Without knowing the actual effectiveness of oil soluble antioxidants, consumers can be exposed to unsafe concentrations. In addition, samples including both lipid soluble antioxidants and water-soluble antioxidants are not correctly rated.

The applicants' unique method of assaying the antioxidant capacity of a sample overcomes the problem associated with oil-based samples by preparing an extraction solution which includes a solubility enhancing compound. One such solubility enhancing compound is cyclodextrin and the derivatives thereof.

Cyclodextrins (CDs) are a group of naturally occurring cage molecules which are built up from α-D-glucose units. Depending on the number of glucose moieties in the ring (6, 7 or 8) they are named α-, β-, and γ-cyclodextrin. CDs are doughnut shaped and can bind a variety of organic 'guest' compounds inside their apolar cavities in aqueous solution. The main driving force for this binding is hydrophobic interactions. There are also numerous compounds chemically derivatized through the hydroxyl groups of CDs of which may be applied to the subject invention.

Cyclodextrins (CDs) contain a relatively hydrophobic (fat-like) central cavity and hydrophilic (water-like) outer surface. This property of cyclodextrin has made it useful as a vehicle for enhancing the solubility of fat-soluble compounds in an aqueous environment. See *Fatty Acid-Cyclodextrin Complexes: Properties and Applications*, J. Incl. Phen. Mol. Recog. Chem., Szente, L., Szejtli, J. 16, 339–354 (1993); *Introduction to Organic Chemistry*, Streitwieser, A.; Heathcock, C. H., 429, Macmillan Publishing Co., Inc. New York (1976), each incorporated herein in their entirety by this reference.

Figure 8:
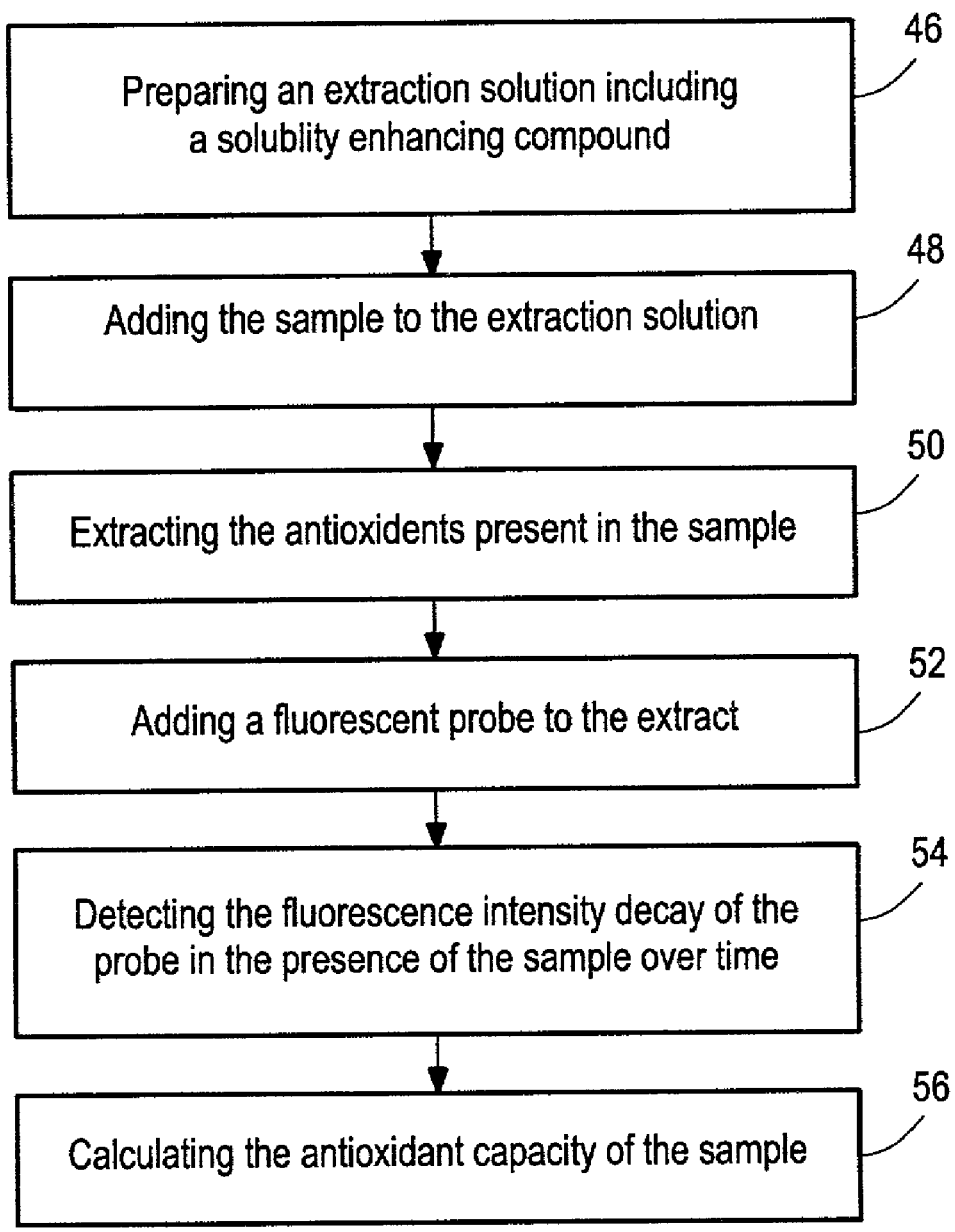
FIG. 8 is a schematic block diagram showing the primary steps associated with the method for assaying the antioxidant capacity of a prepared sample in accordance with the subject invention.

In one embodiment in accordance with the subject invention, the method of assaying the antioxidant capacity of the sample, FIG. 8, includes preparing an extract solution including a solubility enhancing compound, step 46; adding the sample to the extraction solution, step 48; extracting the antioxidants present in the sample, step 50; adding a fluorescence probe to the extract, step 52; detecting the fluorescence intensity decay of the probe in the presence of the sample over time, step 54; and calculating the antioxidant capacity of the sample based on the fluorescence intensity decay of the probe in the presence of the sample, step 56. Ideally, cyclodextrin is the solubility enhancing compound and in one example, randomly methylated β-cyclodextrin (RMCD) is chosen as the solubility enhancing compound. Alternatively, any derivatives of cyclodextrin may be used such as α, β, and γ-cyclodextrin.

As noted supra, lipid soluble antioxidants were not correctly rated because of their insolubility in aqueous media. Moreover, samples with both lipid and water-soluble antioxidants were not correctly rated.

To overcome the problem associated incorrect ORAC antioxidant ratings which result from samples which include both lipid soluble antioxidants and water-soluble antioxidants, the applicants' unique method of assaying the antioxidant capacity of a sample includes an extraction solution which includes both a high-polarity solvent, such as water, a low-polarity solvent, such as acetone, butanone, methanol, acetonitrile and ethanol or other similar low polarity solvents, wherein the solubility enhancing compound enhances the solubility of the lipid-soluble antioxidants which are present in the sample to be tested in the high-polarity solvent. The amount of the high-polarity solvent may be equal to or approximately equal to the amount of the low-polarity solvent. In a preferred embodiment, the solubility enhancing compound is 1% to 40% of the solution.

The applicants' unique method of assaying the antioxidant capacity of the sample which includes a solubility enhancing compound allows for more accurate representation of the actual antioxidant capacity of a sample containing high-levels of lipid-soluble antioxidants as well as lipid soluble antioxidants with water-soluble antioxidants. The applicants' incorporation of cyclodextrin as a solubility enhancing compound to the subject invention significantly increases the ORAC values by enhancing the solubility of the fat-soluble compounds in aqueous environments. Moreover, by using a solubility enhancing compound with a high polarity and low polarity mixture, samples with lipid soluble and water soluble antioxidants can accurately be tested.

Another problem associated with prior art ORAC assays is that a protein probe, such as B-PE is used. As discussed supra, the B-PE probe interacts with the sample in adverse ways which can result in low false readings. This is because B-PE interacts with many polyphenolic compounds resulting non-specific protein bindings. Further, the process of B-PE isolation from *Porphyridium cruetum* itself produces inconsistencies in purity which vary from lot to lot resulting in variable reactivity with free radicals. Moreover, B-PE is highly photosensitive, which is a significant drawback when fluorescence intensity decay is used in an assay because the B-PE will require special handling.

Figure 10:
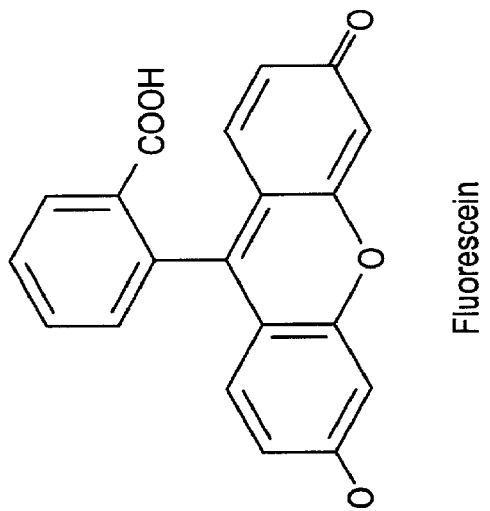
FIG. 10 is a depiction of the structure the non-protein probe fluorescein used for assaying the antioxidant capacity of a sample in accordance with the subject invention.
Figure 9:
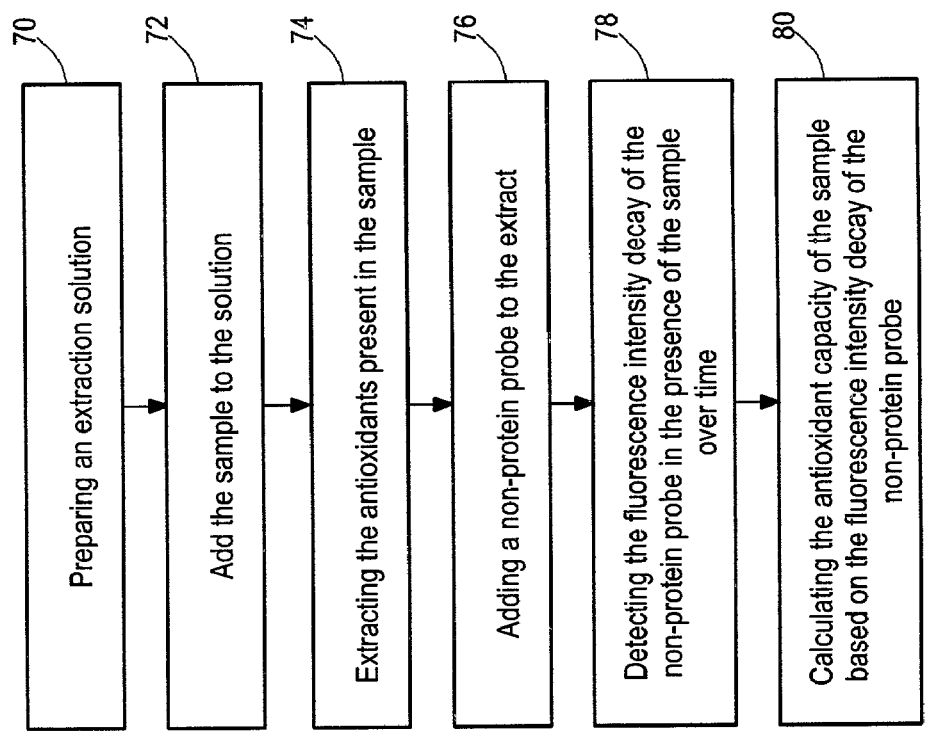
FIG. 9 is schematic block diagram of illustrating the primary steps associated with another embodiment of the method for assaying the antioxidant capacity of a sample in accordance with the subject invention.

In sharp contrast, the applicants' preferred method of assaying the antioxidant capacity of the sample overcomes the problems associated with a protein based fluorescence probe by using a non-protein probe. The unique method of assaying the antioxidant capacity of a sample in accordance with the subject invention includes preparing an extract solution, step 70, FIG. 9; adding the sample to the solution, step 72; extracting the antioxidants present in the sample, step 74; adding a non-protein probe to the extract, step 76; detecting the fluorescence intensity decay of the non-protein probe in the presence of the sample over time, step 78; and calculating the antioxidant capacity of the sample based on the fluorescence intensity decay of the non-protein probe in the presence of the sample, step 80. In one example, the non-protein probe is a hydrogen atom donor such as fluorescein, 3',6'-dihydroxyspiro[isobenzofuran-1(3H), 9'[9H]-xanthen]-3-one, as shown in FIG. 10. Other suitable derivatives of fluorescein may also be used.

The unique non-protein probe, when used in accordance with the subject invention, does not interact with the sample because fluorescein, unlike B-PE, does not interact with polyphenolic compounds which can cause non-specific protein bindings. Moreover, since fluorescein is not manufactured from a microorganism, it does not vary in purity from lot to lot like protein probes. Moreover, fluorescein is not photosensitive and requires no special handling.

Figure 12:
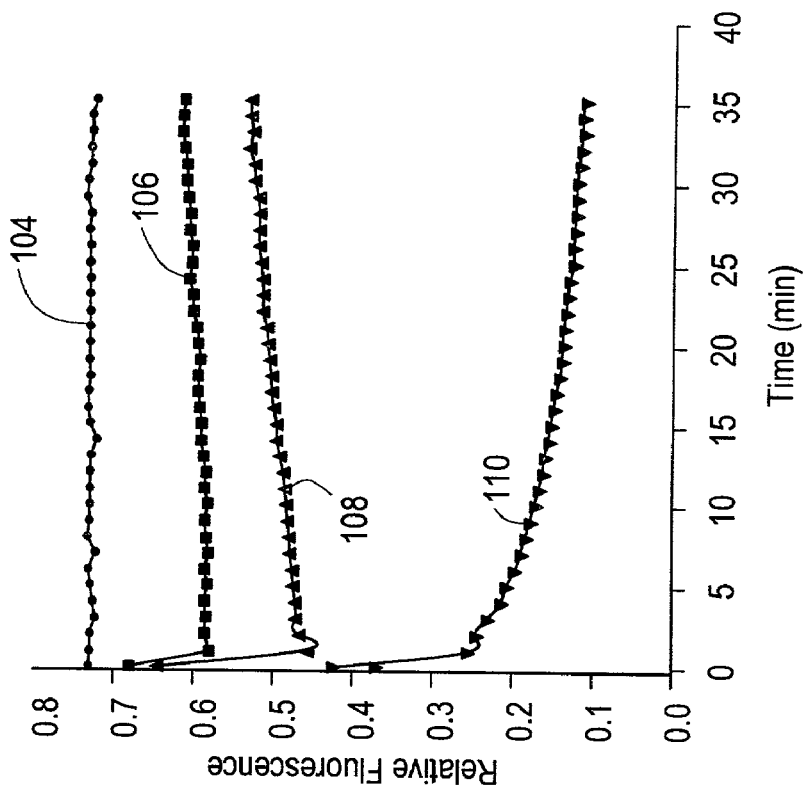
FIG. 12 is a graphical representation showing the strong interaction between a protein probe B-PE and a sample.
Figure 11:
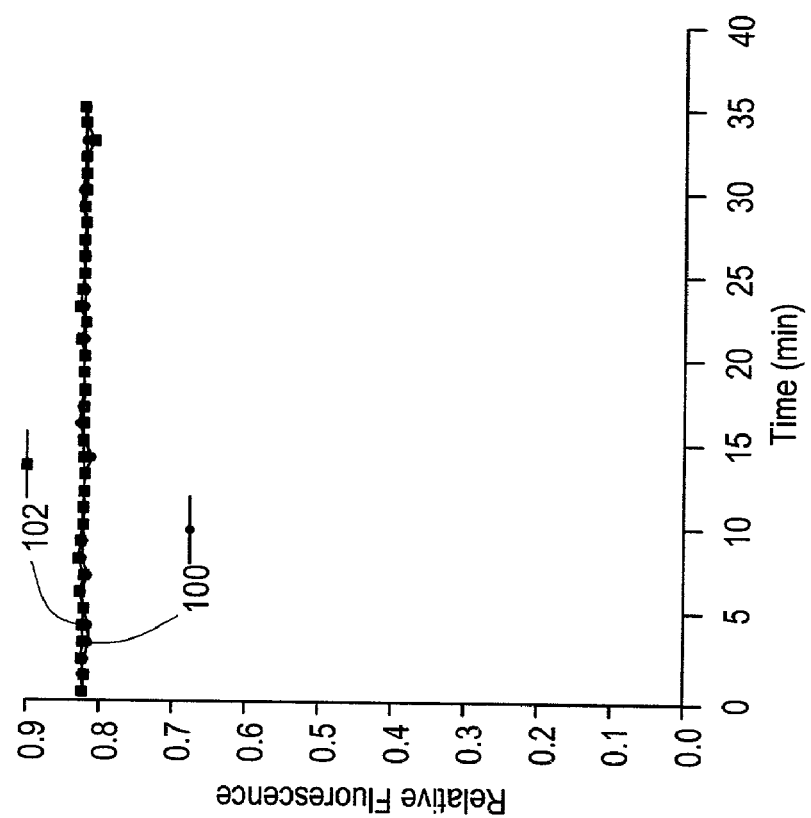
FIG. 11 is a graphical representation showing how there is no interaction between the non-protein probe and the sample in accordance with the subject invention.

A comparison of the binding properties of fluorescein and B-PE probes is shown in FIGS. 11 and 12. As shown in FIG. 11, non-protein probe fluorescein 100, when used in accordance with the subject invention, does not interact with Grape Seed Extract (GSE) 102, which is known to possess strong protein binding properties. In sharp contrast, the B-PE protein probe 104, FIG. 12, strongly binds with the GSE samples 106, 108, and 110.

Tables 1–3 below summarize the ORAC values of 16 chemicals and various samples measured using fluorescein probe in accordance with the subject invention and B-PE probes respectively.

TABLE 1

Relative ORAC Values of Chemicals with Antioxidant Activities*

| Compounds | $ORAC_{FL}$ | $ORAC_{B-PE}$ | Ratio* |
|---|---|---|---|
| Caffeic Acid | 4.37 ± 0.24 | 1.40 ± 0.09 | 3.12 |
| Chlorogenic Acid | 3.14 ± 0.19 | 1.90 ± 0.12 | 1.65 |
| Coumaric Acid | 2.95 ± 0.24 | 1.45 ± 0.03 | 2.03 |
| Quercetrin | 5.87 ± 0.49 | 2.70 ± 0.18 | 2.15 |
| Genistein | 5.93 ± 0.45 | 2.3 ± 0.16 | 2.57 |
| Glutathione | 0.62 ± 0.02 | 0.32 ± 0.01 | 1.94 |
| Rutin | 4.28 ± 0.25 | 1.95 ± 0.21 | 2.19 |
| Quercetin | 4.38 ± 0.22 | 2.07 ± 0.05 | 2.11 |
| Vitamin C | 0.95 ± 0.02 | 0.43 ± 0.03 | 2.21 |

*ORAC values are expressed as relative Trolox equivalent calculated based on equation 2 (n > 3)

TABLE 2

$ORAC_{FL}$ and $ORAC_{PE}$ Values for Biological Fluids and Beverages*

| Sample | $ORAC_{FL}$ | $ORAC_{PE}$ | $ORAC_{FL}/ORAC_{PE}$ |
|---|---|---|---|
| Urine | 1542 ± 178 | 926 ± 133 | 1.67 |
| Whole Serum | 7780 ± 467 | 3383 ± 278 | 2.30 |
| Serum (protein free) | 347 ± 5.63 | 186 ± 9.11 | 1.87 |
| Blueberry Juice | 23748 ± 1555 | 7511 ± 683 | 3.16 |
| Bilberry Juice | 34659 ± 2069 | 12507 ± 893 | 2.77 |
| Grape Juice | 31441 ± 1821 | 12124 ± 912 | 2.59 |
| Raspberry Juice | 54034 ± 2863 | 23056 ± 1800 | 2.34 |
| Black Tea | 17267 ± 441 | 8714 ± 213 | 1.89 |

*ORAC values are expressed as micromole Trolox equivalent per liter (n > 3)

TABLE 3

$ORAC_{FL}$ and $ORAC_{PE}$ of Various Natural Products Extracts*

| Sample | $ORAC_{FL}$ | $ORAC_{PE}$ | $ORAC_{FL}/ORAC_{B-PE}$ |
|---|---|---|---|
| Bilberry | 2646 ± 190 | 1283 ± 144 | 2.06 |
| Elderberry | 2221 ± 164 | 1174 ± 182 | 1.89 |
| Red Wine Extract | 6942 ± 669 | 2194 ± 105 | 3.16 |
| Grape Seeds Extract A | 11889 ± 234 | 3516 ± 135 | 3.38 |
| Grape Seeds Extract B | 11681 ± 923 | 2989 ± 368 | 1.89 |

*$ORAC_{FL}$ and $ORAC_{PE}$ values are expressed as micromole Trolox equivalents per gram (n > 3).

As shown above, the applicants' unique application of the non-protein probe fluorescein in accordance with the subject invention exhibits distinct advantage over the prior art protein probe B-PE. Because there is no interaction between the non-protein probe fluorescein and the sample which would lower the measured ORAC value, the actual measured ORAC values of the antioxidant sample is significantly more accurate (higher) than prior art techniques which use B-PE.

Figure 14:
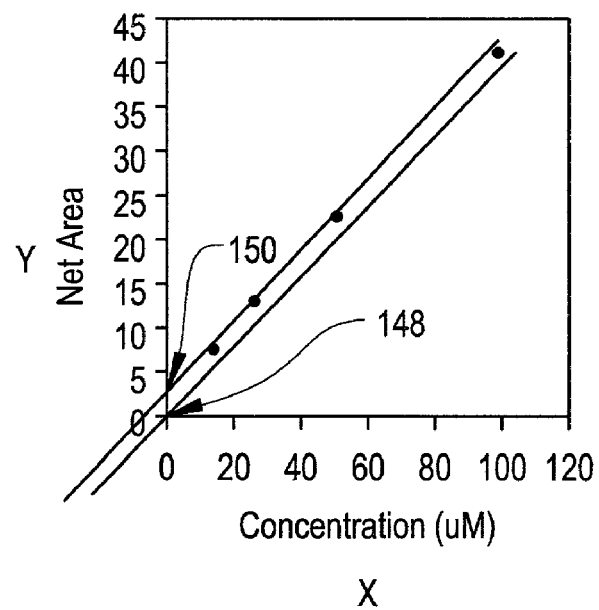
FIG. 14 is a graphical representation showing the calculated net area under the curve versus the concentration of one standard compared to the plurality of standards in accordance with the subject invention.

Another problem with prior art ORAC assays is that only one standard was used. When only one standard is used, calculating the antioxidant capacity of the sample is based on the fluorescence intensity decay of the probe in both the sample and the standard which incorrectly assumes a direct ratio between the antioxidant capacity of the standard and the sample. That is, typical prior art use $$Y(\mu M) = a(\text{intercept}) + bX(\text{net area}) \tag{3}$$

to calculate the concentration of the sample and assume intercept (a) is zero, as shown by arrow 148, FIG. 14. For example, in the prior art, if the concentration of the standard is known ($Y_{standard}$), and the AUC of the standard ($X_{standard}$) is the measured and calculated using equation (1) above, and the AUC of the sample ($X_{sample}$) is measured and calculated using equation (1), the desired concentration of the sample ($Y_{sample}$) is found by assuming (a) is zero and using the ratio of:

$$Y_{Standard}/Y_{sample} = X_{standard}/X_{sample} \tag{4}$$

and solving for $Y_{sample}$. This however, as noted above, assumes the intercept of equation (3) is zero, when in fact it is not. $Y_{sample}$ in then used in equation (2) above and an erroneous ORAC value is calculated.

The applicants' invention overcomes this inaccuracy and false assumption by employing multiple standards at different known concentrations, hence solving (a) of equation (3). Thereafter, the exact concentration of the sample can be found and applied to equation (2) above, yielding a more accurate ORAC value for the sample being tested.

Figure 13:
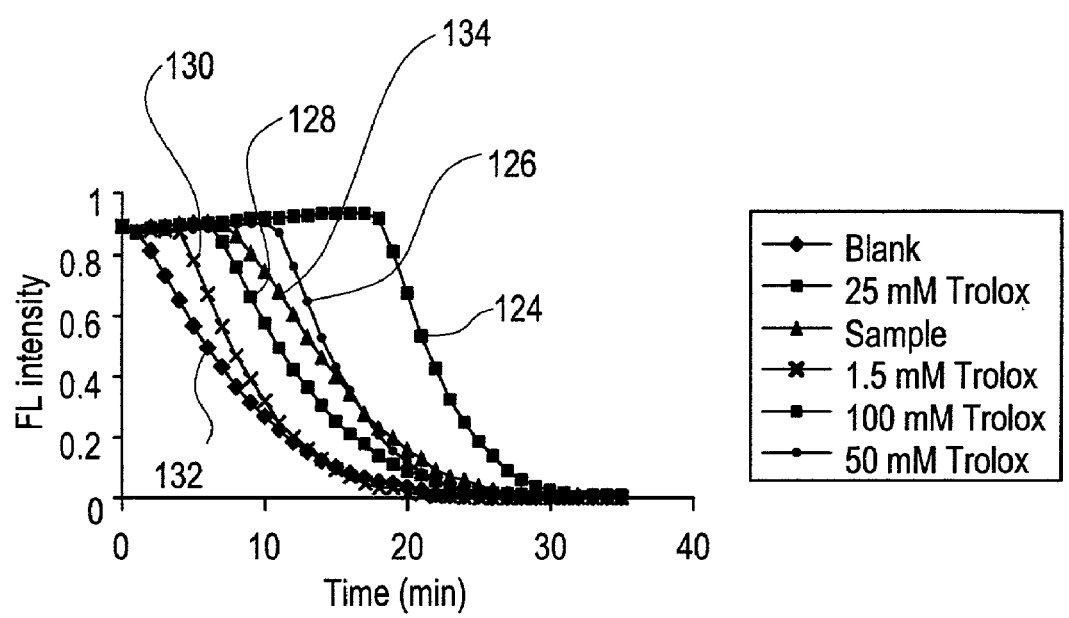
FIG. 13 is graphical representation showing the fluorescent intensity decay of four standards as used in one embodiment in accordance with the subject invention.
Figure 15:
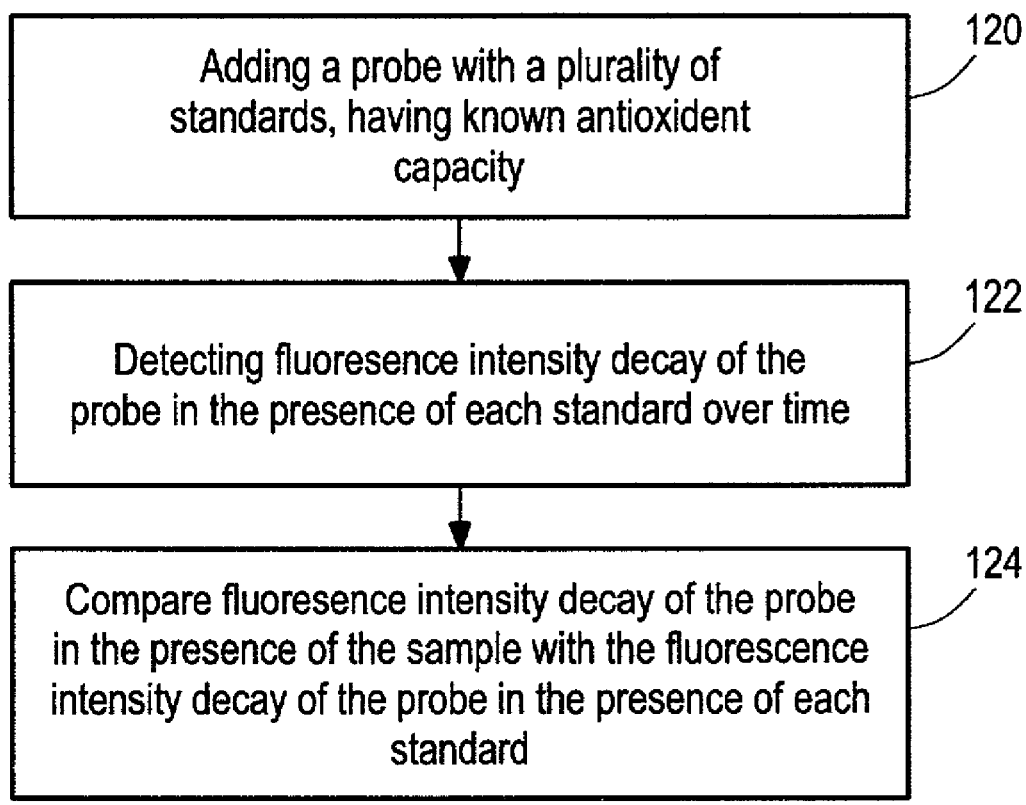
FIG. 15 is a schematic block diagram illustrating the primary steps associated with another embodiment of the method for assaying the antioxidant capacity of a sample in accordance with the subject invention.

In one preferred embodiment in accordance with the subject invention, the method for assaying the antioxidant capacity of a sample includes adding a probe which includes a plurality of standards having a known antioxidant capacity, step 120, FIG. 15, which is supplementary to step 52, FIG. 3. Thereafter, the fluorescence intensity decay of the probe is detected in the presence of each standard, step 122; and a comparison of the fluorescence intensity of the probe in the presence of the sample with the fluorescence intensity decay of the probe in the presence of each standard is performed, step 124. As shown in FIG. 13, four standards are used in addition to a blank standard. In one example, standards 124, 126, 128, and 130 and blank 132 are used. Preferably, the standards 124, 126, 128, and 130 are Trolox at concentrations of 100 μM, 50 μM, 25 μM and 12.5 μM, respectively. FIG. 10 illustrates the fluorescence decay curves of standards 124–130, as well as blank 132. These AUC of sample 134, standards 124–130, and blank 132 is calculated using equation (1) above. However, in accordance with the subject invention, standards 124, 126, 128, and 130 are applied to equation (3) and the exact value of intercept (a) is calculated. Thereafter, the exact concentration of sample 134 can be calculated and applied to equation (2) above. The result is a significantly more accurate ORAC value because the assumption that intercept (a) of equation (3) is zero is not made as shown by arrow 150, FIG. 14. Table 4 below summarizes the trolox calibration curve including the coalition coefficient ($R^2$), slope (b) and intercept (a) of 9 runs of calculating the exact intercept of the standard in accordance with the subject invention.

TABLE 4

Summary of Trolox Calibration Curve [Y (μM) = a + bX(net area)]

| Run No. | $R^2$ | Slope (b) | Intercept (a) |
|---|---|---|---|
| 1 | 0.9994 | 2.5368 | −2.174 |
| 2 | 0.9993 | 2.7390 | −4.690 |
| 3 | 0.9981 | 2.6947 | −5.109 |
| 4 | 0.9973 | 2.5291 | −3.846 |
| 5 | 0.9928 | 2.2331 | 1.361 |
| 6 | 0.9978 | 2.8868 | −3.788 |
| 7 | 0.9981 | 2.6288 | −3.012 |
| 8 | 0.9987 | 2.5297 | −2.589 |
| Average | 0.9977 | 2.5846 | −2.861 |
| Acceptable Criteria | ≧0.9900 | NA | NA |

By using four standards instead of one, the exact correlation between the antioxidant capacity of the sample and each standard can be made. Accordingly, by using the calculated intercept the correct concentration of the sample can be found and a more accurate representation of the actual antioxidant capacity of the sample can be calculated.

Still another problem with the prior art ORAC assay is that perchloric acid was added to biological samples to separate the proteins from the samples. However, perchloric acid itself is a strong oxidizing agent and yields false low antioxidant capacity readings.

In a preferred embodiment of the subject invention, a non-chemical means is used to remove the proteins from the sample. The biological fluids to be tested are filtered through a microcon filter tube with cut-off molecular weight of 2500 g/mol. Ideally, 1.0 mL of the biological fluid to be tested is added to a microcon filter tube and centrifuged at 1400 rpm for up to 1 hour at 4° C. The liquid at the bottom of the tube is collected for ORAC analysis with the COBAS FARA II analyzer or FL600 microplate fluorescence reader.

The applicants' unique method of using non-chemical means to remove the biological sample prevents percloric acid, or any type of reagent, to act as and oxidizing agent which falsely lowers antioxidant capacity readings of a sample. In accordance with the subject invention, the unique ultra filtration technique employed eliminates using any reactive reagents thereby eliminating any possible interaction of the reagents with the sample. The result is a more accurate antioxidant capacity reading.

Finally, prior art ORAC procedures involve a long dwell time of up to seventy-five minutes. In a preferred embodiment of the subject invention, the method for assaying the antioxidant capacity of a sample as set forth herein significantly reduces the dwell time by increasing the concentration of the free radical generator precursor to the probe/extract mixture. Ideally, the free radical generator precursor is AAPH at a concentration of the above 4 mM. Preferably, the concentrations of the precursor is above 12.8 mM.

In yet another embodiment of the subject invention, a kit for assaying the antioxidant capacity of a sample includes an extraction solution including a solubility enhancing compound to be added to the sample for extracting antioxidants present in the sample and a fluorescent probe added to the extract. The kit may include an extraction solution including a high polarity solvent and a low polarity solvent: the high polarity solvent may be water and the low polarity solvent may be acetone, butanone, methanol acetonitrile or ethanol, and may also include a solubility enhancing compound such as cyclodextrin and the derivatives thereof. The amount of the high polarity solvent may be equal to or approximately equal to the amount of low polarity solvent and the solubility enhancing compound is typically 1% to 40% of the solution. The kit may also include a non-protein probe which is a hydrogen atom donor probe such as fluorescein. In one example, the kit includes a plurality of standards having a known antioxidant capacity so that the fluorescent intensity decay of the probe in the presence of each standard over time can be detected. The four standards may range from 10 μM to 100 μM. Each standard is preferably Trolox. A free radical generator precursor, such as AAPH, may be added to the probe extract mixture. In one example, the concentration of the precursor is above 4 mM, and preferably is 12 mM.

The applicants unique method for assaying the antioxidant capacity of a sample includes a unique solubility enhancing compound which overcome the problems associated with the insolubility of lipids in aqueous media. The unique non-protein probe accurately measures the ORAC value of samples without interacting with the sample, is consistently pure because it is not produced from a microorganism, and is not photosensitive and hence requires no special handling. By using a plurality of standards, more accurate ORAC readings can be found because the calculations include the exact location of the zero intercept. Further, removal of proteins can be accomplished by without using perchloric acid which interacts with the sample. Finally, dwell time of the ORAC assay is significantly reduced by increasing the concentration of AAPH.

EXAMPLES

The following examples are meant to illustrate and not limit the present invention. Unless otherwise stated, all parts therein are by weight.

Example 1

Materials and Methods

Flavonoid compounds and β-phycoerythrin were purchased from Sigma (St. Louis, Mo.). Trolox, ascorbic acid and disodium fluorescein were obtained from Aldrich (Milwaukee, Wis.). 2,2'-azobis (2-amidino-propane) dihydrochloride (AAPH) was purchased from Wako Chemicals USA (Richmond, Va.). Various analyzed samples were also obtained. ORAC analyses were performed on a COBAS FARA II analyzer (Roche Diagnostic System Inc., Branchburg, N.J.; Excitation wavelength=493 nm and emission filter=515 nm).

Ascorbic acid and flavonoids were directly dissolved in acetone/water mixture (50:50, v/v) and diluted with pH 7.4 phosphate buffer for analysis. The solid samples were initially ground in a mechanical mill to produce a fine power; then 0.5 grams were accurately weighed and 20 mL of acetone/water (50:50, v/v) extraction solvent was added. The mixture was shaken at 400 RPM at room temperature on an orbital shaker for one hour. The extracts were centrifuged at 14000 rpm for 15 min, and the supernatant was ready for analysis after appropriate dilution with buffer solution. For liquid samples, a 20 mL aliquot of sample was centrifuged for 15 min and the supernatant was ready for analysis after appropriate dilution. Blood plasma or serum was diluted 100 to 200 fold with pH 7.4 phosphate buffer before analysis. To measure the ORAC in non-protein fraction, protein was removed using 0.5 N perchloric acid (1:1; v:v; plasma:acid), the samples were then centrifuged at 140,000×g for 10 min at 4° C., and the supernatants were removed as the serum nonprotein fractions and appropriately diluted with pH 7.4 phosphate buffer before the analysis.

Peroxyl radical scavenging assay. The COBAS FARA II was programmed to use a two-reagent system (Reaction Mode 3, P-I-SRI-A). The reaction mode pipetted and transferred the sample (20 μL), phosphate buffer (5 μL, 0.75 mM, pH 7.4), and main reagent (365 μL FL, $4.8 \times 10^{-8}$ M) into the main reagent wells of their respective cuvette rotor positions. With spinning of the rotor, the reagents are mixed and incubated for 30 s before recording the initial fluorescence ($f_0$). After the rotor stops spinning, a start reagent (SRI), 8 μL of APPH (0.64M) plus 2 μL of the phosphate buffer is pipetted into the appropriate start reagent well in the cuvette rotor. Next, the analyzer starts spinning, mixing of the sample/FL with AAPH reagent and the oxidative reaction starts. Hence, the sample makes up 5% of the reaction volume, and the final concentrations of FL and AAPH are $4.38 \times 10^{-8}$ M and $1.28 \times 10^{-2}$ M, respectively. Between transfers, both sample and reagent transfer pipettes are washed with clean solution to eliminate sample cross contamination. Fluorescence readings are taken at 0.5 s and then every minute thereafter ($f_1, f_2, f_3 \ldots$) for a duration of 30 min. If the fluorescence of the final reading has not declined by >95% from the first reading, the dilution of sample is adjusted accordingly and the sample is reanalyzed. To determine the maximum voltage for the photomultiplier tube, the AAPH reagent is omitted and is replaced with buffer, and the analysis is run for 10 min. FL and AAPH were prepared in a 0.75 mM phosphate buffer. FL working solution was routinely preincubated in a waterbath at 37° C. for 15 min before loading into the COBAS reagent rack. Phosphate buffer was used as a blank and Trolox concentrations of 12.5, 25, 50, 100 μM were used as standards.

Example 2

Modified Assay for Lipophilic Antioxidants Using Solubility Enhancing Randomly Methylated Cyclodextrin Chemicals and Apparatus. Cyclodextrin derivatives were supplied from Cyclodextrin Technologies Development, Inc. (Gainesville, Fla.). Fluorescein (FL) and Trolox were purchased from Aldrich (Milwaukee, Wis.). 2,2'-azobis (2-amidino-propane) dihydrochloride (AAPH) was obtained from Wako Chemicals USA (Richmond, Va.). γ-Oryzanol was purchased from TCI America (Portland, Oreg.); nutriene (tocotrienols) was obtained from Eastman Chemicals Company (Kingsport, Tenn.). All other standards were commercially available form Sigma or Aldrich. Analyses were performed on a COBAS FARA II analyzer (Roche Diagnostic System Inc., Branchburg, N.J. using an excitation wavelength of 493 nm and an emission filter of 515 nm or alternatively, the sample may be analyzed with a FL600 microplate fluorescence reader (Bio-Tek Instruments, Inc., Winooski, Vt.) with fluorescence filters for an excitation wavelength of 485±20 nm and a emission wavelength of 530±25 nm. The plate reader is ideally controlled by software, such as KC4 3.0 (reversion 29). Sample dilution is accomplished by a Precision 2000 automatic pipetting system managed by software, such as precision power software (version 1.0), Bio-Tek Instruments, Inc., Winooski, Vt. The 96-well polystyrene microplates and covers may be purchased from VWR International, Inc. (Bridgeport, N.J.). High performance Liquid Chromatography (HPLC) and mass spectroscopy conditions are the same as in reference (4).

Samples. Twelve seed oils and fourteen essential oils were obtained in house.

Sample Preparation. Approximately 0.5 g of sample was dissolved in 20 mL acetone. An aliquot of sample solution was appropriately diluted with 7% cyclodextrin solvent made in 50% acetone-water mixture (v/v) and was shaken for 1 hour at room temperature on an orbital shaker. The sample solution was ready for analysis after further dilution with 7% cyclodextrin solution.

The automated ORAC assay was carried out on a COBAS FARA II spectrofluorometric centrifugal analyzer. In the final assay mixture (0.4 mL total volume), FL ($4.38 \times 10^{-8}$ M) was used as a target of free radical attack and AAPH ($1.28 \times 10^{-2}$ M) as a peroxyl radical generator. Trolox solutions (12.5, 25, 50, 100 μM) were used as control standards. The analyzer was programmed to record the fluorescence of FL every minute after addition of AAPH. All measurements were expressed relative to the initial reading. Final results were calculated using the differences of areas under the FL decay curves between the blank and a sample. These results were expressed as micromole Trolox equivalents (TE) per gram or liter.

In accordance with the subject invention, ORAC values were measured for several plant seed oils and essential oils. The antioxidant activity of the plant seed oil varies greatly from several hundred μmolTE/liter (Olive Divanci) to over fifty thousand μmolTE/liter (Caraway). The Essential oils have impressively high ORAC values per gram bases. For example Myrrh oil has over 4000 μmolTE/g, which is over three times higher than that of pure α-tocopherol (1162 μmolTE/g).

Using randomly methylated β-cyclodextrin as solubility enhancer a validated assay for oxygen radical absorbance capacity of lipophilic antioxidants ($ORAC_{lipo}$) was established. The $ORAC_{lipo}$ method is robust, reliable and sensitive. The precision determined at each concentration level does not exceed 15% coefficient of variation. The limit of detection is 5 µM and the limit of quantitation is 12.5 µM. Steric hindrance around phenol groups may have negative effect on ORAC values of tocopherols. The method has been applied in evaluation of antioxidant activity of plant oils.

Example 3

Using a Plurality of Standards

Trolox concentrations of 20, 40, 75 µM were used as QC samples. Samples and Trolox calibration solutions were always analyzed in duplicate in a "forward-then-reverse" order as follows: blank, 12.5 µM Trolox, 25 µM Trolox, 50 µM Trolox, 100 µM Trolox, QC, sample 1 . . . sample 1, QC, 100 µM, 50 µM, 25 µM, 12.5 µM, blank. This arrangement can correct for possible errors due to the signal drifting associated with the different positions of the same sample. Nine samples can be tested in duplicate in each analysis. The final ORAC values are calculated by using a regression equation between the Trolox concentration and the net area under the FL decay curve and are expressed as Trolox equivalents as micromole per liter or per gram. The area under curve (AUC) is calculated as shown above in equations (1) and (2).

Characterization of Fluerescein (FL) oxidized products. FL ($4.38 \times 10^{-7}$ M) was incubated at 37° C. for 20 min with AAPH ($1.28 \times 10^{-2}$ M) at pH 7.4, and the reaction mixture was analyzed by LC/MS. Chromatographic analyses were performed on an HP 1100 series HPLC equipped with an autosampler/injector, binary HPLC pump, column heater, diode array detector, fluorescence detector and HP ChemStation for data collection and manipulation. Reverse phase separation was performed on a Zorbax C18 column (2.1× 150 mm, 3 µm) at 37° C. UV detection was recorded at 278 nm and for fluorescence detection, the excitation wavelength was 491 nm and the emission wavelength was 515 nm. The binary mobile phase consisted of (A) water, acetonitrile, acetic acid (89:9:2) (B) water, and acetonitrile (20:80). The separation was performed using a linear gradient from 0% to 30% B in 30 min. The structural information was obtained using an LCQ ion trap mass spectrometer (Thermoquest, San Jose, Calif.) equipped with an API chamber and an ESI source. The ionization mode was negative mode, Aux gas and Sheath gas were set to 90 and 23 units, respectively. An ionization reagent of 1.5 mM ammonium hydroxide was added at a rate of 0.05 mL/min through a Tee device by using a secondary HPLC pump before the API chamber. Fluerescein disodium was used as a standard for calibrating the system. As shown in FIG. 13, the HPLC output monitored at 278 nm and fluorescence at 493 nm excitation and 515 nm emissions of fluorescein and oxidized products in the presence of AAPH.

The linear relationship between the net area and antioxidant concentration was evaluated by the inventors hereof using Trolox, black tea leaves, blueberry extracts and grape skin extracts at different concentrations. The results are summarized in Table 5 below, showing the net areas corresponding to the different concentrations of black tea leaves, elderberry extract and grape seed extract and the calculated ORAC values. All analyzed samples in the various forms demonstrate a good linear relationship between the net area and concentration. Trolox was used as a calibration standard. The limit of quantitation (LOQ) and the limit of detection (LOD) are 12.5 and 5 µM, respectively. An acceptable correlation of coefficient was ≧0.99.

TABLE 5

Net Area Corresponding to Different Concentrations of Extracts from Tea, Blueberry and Grape Skins.

| Natural Products | Conc. (mg/L) | Net Area | ORAC* |
|---|---|---|---|
| Black Tea leaves | 8 | 5.92 | 1586 |
|  | 16 | 10.81 | 1566 |
|  | 32 | 21.51 | 1629 |
| Blueberry Extracts | 5 | 5.73 | 2441 |
|  | 10 | 11.32 | 2635 |
|  | 20 | 22.98 | 2792 |
| Grape Skin Extracts | 1.2 | 8.34 | 15675 |
|  | 2.4 | 15.63 | 15521 |
|  | 4.8 | 29.89 | 14714 |

*ORAC values are expressed as Trolox Equivalents per gram. The RSD for average value of each sample is less than 15%.

Example 4

High Throughput ORAC Assay Using Multi-Channel Liquid Handling System With Microplate Fluorescence Reader Chemicals and Apparatus. Trolox and fluorescein disodium were obtained from Aldrich (Milwaukee, Wis.). 2,2'-azobis(2-amidino-propane) dihydrochloride (AAPH) was purchased from Wako Chemicals USA (Richmond, Va.). B-Phycoerythrin (B-PE) and 15 phenolic compounds were obtained from Sigma Co. (St. Louis, Mo.). Coffee powder, rosemary extract, strawberry extract and grape juice were obtained in house. Plasma was withdrawn from 3 volunteers at Brunswick Laboratories. A FL600 microplate fluorescence reader (Bio-Tek Instruments, Inc., Winooski, Vt.) was used with fluorescence filters for an excitation wavelength of 485±20 nm and an emission wavelength of 530±25 nm. The plate reader was controlled by software KC4 3.0 (reversion 29). Sample dilution was accomplished by a precision 2000 automatic pipetting system managed by precision power software (version 1.0) (Bio-Tek Instruments, Inc., Winooski, Vt.). The 96-well polystyrene microplates and the covers were purchased from VWR International Inc (Bridgeport, N.J.). A COBAS FARA II analyzer (Roche Diagnostic System Inc., Branchburg, N.J.) was used for a comparison study.

Automated Sample Preparation. The automated sample preparation was performed using a Precision 2000. The layout of the deck of the Bio-Tek Precision 2000 is illustrated in FIG. 4. As shown, the 250 µL pipette racks were placed at station A and D. Station B was the reagent vessel in which 50 mL $5.84 \times 10^{-5}$ mM FL was placed in reagent holder 1 and 50 ml 75 mM phosphate buffer (pH 7.4) was added in reagent holder 2. A 96-well polypropylene plate (maximum well volume 320 µL) was placed at station C for sample dilution. The initial addition of samples into the 96-well plate at station C was done by manual mode using an 8-channel pipette. Briefly, 200 µL 75 mM phosphate buffer (blank) was dispensed into Column 11 (wells A11-H11). The Trolox standard solution was added into column 12 (wells A12-H12) as follows: 6.25 µM (A12), 12.5 µM (B12), 25 µM (C12), 50 µM (D12), 50 µM (E12), 25 µM (F12), 12.5 µM (G12), 6.25 µM (H12). Then 8 samples were pipetted into column 1 (wells A1-H1) and column 6 (wells A6-H6), respectively. The sample series dilution sequence was programmed and controlled by the precision power software (version 1.0). An initial 1:40 dilution was performed followed by consecutive 1:2, 1:2 and 1:2 dilutions, this would give a series of 1:40, 1:80, 1:160, and 1:320 dilutions. Any other desired lower dilution can be obtained by simply performing a series of 1:4 or 1:8 dilutions after initial 1:40 dilution. Care was taken to ensure homogeneity of each dilution by thorough mixing at each stage through repeated aspiration and dispensing programmed by the precision power software. There is no dilution needed for Trolox standards and blank. FIG. 5 illustrates the layout for the plate at station C. FIG. 6 shows the layout of the 96-well plate used for a typical measurement.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims.

What is claimed is:

1. A method of assaying the antioxidant capacity of a sample, the method comprising:
    preparing an extraction solution including a solubility enhancing compound comprising cyclodextrine and derivatives thereof;
    adding the sample to the extraction solution;
    extracting the antioxidants present in the sample;
    adding a fluorescent probe to the extract;
    detecting the fluorescence intensity decay of the probe in the presence of the sample over time; and
    calculating the antioxidant capacity of the sample based on the fluorescence intensity decay of the probe in the presence of the sample.

2. The method of claim 1 in which the solution includes a high polarity solvent and a low polarity solvent and wherein the solubility enhancing compound enhances the solubility of lipid soluble antioxidants present in the sample in the high polarity solvent.

3. The method of claim 2 in which the high polarity solvent is water.

4. The method of claim 2 in which the low polarity solvent is selected from the group consisting of acetone, butane, methanol, acetonitrile, and ethanol.

5. The method of claim 2 in which the amount of the high polarity solvent is equal to or approximately equal to the amount of low polarity solvent.

6. The method of claim 1 in which the solubility enhancing compound is 1% to 40% of the solution.

7. The method of claim 1 in which the probe is a non-protein probe.

8. The method of claim 7 in which the non-protein probe is a hydrogen atom donor probe.

9. The method of claim 8 in which the hydrogen atom donor probe is fluorescein and derivatives thereof.

10. The method of claim 1 further including the steps of:
    adding the probe to a plurality of standards each having a known antioxidant capacity; and
    detecting the fluorescence intensity decay of the probe in the presence of each standard over time.

11. The method of claim 10 in which the calculating step includes comparing the fluorescence intensity decay of the probe in the presence of sample with the fluorescence intensity decay of the probe in the presence of each standard.

12. The method of claim 10 in which there are four standards.

13. The method of claim 10 in which the concentration of the standards ranges from 1 µM to 100 µM.

14. The method of claim 13 in which each standard is 6-hydroxy-2,5,7,8-tetramethylchroman-2-carboxylic acid.

15. The method claim 1 in which the preparation step further includes removing any proteins present in the sample.

16. The method of claim 15 in which the step of removing any proteins involves using non-chemical means to remove the proteins.

17. The method of claim 16 in which the non-chemical means include using an ultra-filtration technique.

18. The method of claim 1 further including adding a free radical generator precursor to the probe/extract mixture.

19. The method of claim 18 in which the precursor is 2.2'-azobis(2-amidino-propane)dihydrochloride (AAPH).

20. The method of claim 19 in which the concentration of the precursor is above 4 µM.

21. The method of claim 20 in which the concentration of the precursor is 12.8 mM.

22. The method of claim 1 in which a microplate fluorescence reader is used to detect the intensity decay of the probe in the presence of the sample over time.

23. The method of claim 1 in which an automatic pipetting system is used to dilute the sample.

24. The method of claim 23 in which the sample is automatically diluted with a buffer solution to a concentration of sample to buffer in the range of 1:2 to 1:20,480.

25. The method of claim 23 in which the automatic pipetting system adds the fluorescent probe to the sample.

26. The method of claim 23 in which the automatic pipetting system adds the fluorescent probe to the plurality of standards.

27. The method of claim 23 in which the automatic pipetting system adds the free radical generator precursor to the probe/extract mixture.

28. A method of assaying the antioxidant capacity of a sample, the method comprising:
    preparing an extraction solution;
    adding the sample to the solution;
    extracting the antioxidants present in the sample;
    adding a non-protein probe to the extract;
    detecting the fluorescence intensity decay of the non-protein probe in the presence of the sample over time; and
    calculating the antioxidant capacity of the sample based on the fluorescence intensity decay of the non-protein probe in the presence of the sample.

29. The method of claim 28 in which the extraction solution includes a solubility enhancing compound comprising cyclodextrine and derivatives thereof.

30. The method of claim 29 in which the solubility enhancing compound is 1% to 40% of the solution.

31. The method of claim 28 in which the extraction solution includes a high polarity solvent and a low polarity solvent.

32. The method of claim 31 in which the high polarity solvent is water.

33. The method of claim 31 in which the low polarity solvent is selected from the group consisting of acetone, butanone, methanol, acetonitrile, methylene chloride, 1,2-dichloroethane, and ethanol.

34. The method of claim 31 in which the amount of the high polarity solvent is equal to or approximately equal to the amount of low polarity solvent.

35. The method of claim 28 in which the non-protein probe is a hydrogen atom donor probe.

36. The method of claim 35 in which the hydrogen atom donor probe is fluorescein.

37. The method of claim 28 further including the steps of:
adding the non-protein probe to a plurality of standards each having a known antioxidant capacity, and
detecting the fluorescence intensity decay of the probe in the presence of each standard over time.

38. The method of claim 37 in which the calculating step includes comparing the fluorescence intensity decay of the probe in the presence of the sample with the fluorescence intensity decay of the probe in the presence of each standard.

39. The method of claim 37 in which there are four standards.

40. The method of claim 37 in which the concentration of the standards ranges from 10 µM moles to 100 µM.

41. The method of claim 37 in which each standard is 6-hydroxy-2,5,7,8-tetramethylchroman-2-carboxylic acid.

42. The method claim 28 in which the preparation step further includes removing any proteins present in the sample.

43. The method of claim 42 in which the step of removing any proteins involves using non-chemical means to remove the proteins.

44. The method of claim 43 in which the non-chemical means include using an ultra-filtration technique.

45. The method of claim 28 further including adding a free radical generator precursor to the probe/extract mixture.

46. The method of claim 45 in which the precursor is 2.2'-azobis(2-amidino-propane)dihydrochloride (AAPH).

47. The method of claim 46 in which the concentration of the precursor is above 4 mM.

48. The method of claim 46 in which the concentration of the precursor is 12.8 mM.

49. The method of claim 28 in which a microplate fluorescence reader is used to detect the intensity decay of the probe in the presence of the sample over time.

50. The method of claim 28 in which an automatic pipetting system is used to dilute the sample.

51. The method of claim 50 in which the sample is automatically diluted with a buffer solution to a concentration of sample to buffer in the range of 1:2 to 1:20,480.

52. The method of claim 50 in which the automatic pipetting system adds the non-protein fluorescent probe to the sample.

53. The method of claim 50 in which the automatic pipetting system adds the fluorescent probe to the plurality of standards.

54. The method of claim 50 in which the automatic pipetting system adds the free radical generator precursor to the probe/extract mixture.

55. A method of assaying the antioxidant capacity of a sample, the method comprising:
preparing an extraction solution including a solubility enhancing compound comprising cyclodextrine and derivatives thereof;
adding the sample to the extraction solution;
extracting the antioxidants present in the sample;
adding a fluorescent probe to the extract;
adding a free radical generator precursor to the extract;
detecting the fluorescence intensity decay of the probe in the presence of the sample over time; and
calculating the antioxidant capacity of the sample based on the fluorescence intensity decay of the probe in the presence of the sample.

56. The method of claim 55 in which the precursor is 2.2'-azobis(2-amidino-propane)dihydrochloride (AAPH).

57. The method of claim 55 in which the concentration of the precursor is above 4 µM.

58. The method of claim 57 in which the concentration of the precursor is 12.8 mM.

* * * * *